US012564737B2

(12) United States Patent
Ramamurthy et al.

(10) Patent No.: US 12,564,737 B2
(45) Date of Patent: Mar. 3, 2026

(54) RAPID CALCULATION OF PARAMETERS FOR DELIVERING ULTRASOUND ENERGY TO SELECTED LOCATIONS IN THE BRAIN

(71) Applicant: Cordance Medical Inc., Mountain View, CA (US)

(72) Inventors: Bhaskar S. Ramamurthy, Los Altos, CA (US); Mallika Keralapura, San Jose, CA (US); John Douglas Marshall, Los Gatos, CA (US)

(73) Assignee: Cordance Medical Inc., Mountain View, CA (US)

( * ) Notice: Subject to any disclaimer, the term of this patent is extended or adjusted under 35 U.S.C. 154(b) by 0 days.

(21) Appl. No.: 18/358,330

(22) Filed: Jul. 25, 2023

(65) Prior Publication Data

US 2024/0042242 A1 Feb. 8, 2024

Related U.S. Application Data

(60) Provisional application No. 63/393,045, filed on Jul. 28, 2022.

(51) Int. Cl.
*A61N 7/00* (2006.01)
*G16H 20/40* (2018.01)

(52) U.S. Cl.
CPC .............. *A61N 7/00* (2013.01); *G16H 20/40* (2018.01); *A61N 2007/0004* (2013.01); *A61N 2007/0078* (2013.01)

(58) Field of Classification Search
CPC .............. A61N 7/00; A61N 2007/0004; A61N 2007/0078; G16H 20/40
See application file for complete search history.

(56) References Cited

U.S. PATENT DOCUMENTS

2004/0122323 A1* 6/2004 Vortman .................. A61N 7/02
600/459
2008/0269607 A1* 10/2008 Ishida ...................... A61N 7/02
600/439
(Continued)

FOREIGN PATENT DOCUMENTS

CN 113577582 A 11/2021
WO 2021014221 A1 1/2021
(Continued)

OTHER PUBLICATIONS

International Search Report and Written Opinion for PCT/US2023/028658 mailed Dec. 18, 2023 15 pages.

*Primary Examiner* — Keith M Raymond
*Assistant Examiner* — Adam D. Kolkin
(74) *Attorney, Agent, or Firm* — Kilpatrick Townsend & Stockton LLP

(57) ABSTRACT

Systems and methods for rapid calculation of parameters for delivering ultrasound energy to selected locations in the brain. An example method for delivering ultrasound energy to a region of a blood-brain barrier may comprise generating a model of the region of the blood-brain barrier and surrounding tissues. The method may also comprise determining a plurality of intermediate parameters by simulating acoustic paths of a plurality of ultrasound beams propagating from the region of the blood-brain barrier to a plurality of locations. The method may also comprise determining transmission parameters for ultrasound beams to be emitted from a plurality of ultrasound transducers based on the intermediate parameters and measured locations of the ultrasound transducers.

17 Claims, 12 Drawing Sheets

(56)         References Cited

U.S. PATENT DOCUMENTS

| | | | | |
|---|---|---|---|---|
| 2013/0158577 | A1* | 6/2013 | Mahon ................. | A61B 5/0036 |
| | | | | 606/169 |
| 2015/0359603 | A1* | 12/2015 | Levy ........................ | A61N 7/02 |
| | | | | 703/2 |
| 2019/0175954 | A1 | 6/2019 | Levy et al. | |
| 2019/0183457 | A1 | 6/2019 | Ramamurthy | |
| 2019/0184204 | A1 | 6/2019 | Ramamurthy | |
| 2019/0308038 | A1* | 10/2019 | Prus .................... | A61B 8/4488 |
| 2023/0082109 | A1 | 3/2023 | Ramamurthy et al. | |

FOREIGN PATENT DOCUMENTS

| | | | |
|---|---|---|---|
| WO | 2021154730 | A1 | 8/2021 |
| WO | 2022032283 | A2 | 2/2022 |

\* cited by examiner

RAPID CALCULATION OF PARAMETERS FOR DELIVERING ULTRASOUND ENERGY TO SELECTED LOCATIONS IN THE BRAIN

REFERENCE TO RELATED APPLICATIONS

This application claims priority from, and for the purposes of the United States the benefit under 35 USC 119 in relation to, U.S. patent application No. 63/393,045 filed 28 Jul. 2022, which is hereby incorporated herein by reference.

FIELD

The present disclosure relates to ultrasound systems and methods for delivering ultrasound energy to locations in a brain. Some embodiments provide systems and methods for rapidly determining transmission parameters for treatment ultrasound energy (also referred to herein as treatment ultrasound beams).

BACKGROUND

Drugs are an important treatment modality for a range of diseases affecting the brain including brain cancers. Treatment of diseases of the brain is challenging in part due to the structure of the blood-brain barrier. The blood-brain barrier separates circulating blood from other brain tissue, and has a highly selective permeability. This barrier prevents about 98% of small molecules and nearly 100% of large molecules from entering the brain from the bloodstream. This makes it difficult to transport drugs to various tissues of the brain, e.g. to tumor sites.

The blood-brain barrier can be caused to open in certain regions by delivering ultrasound energy to those regions.

There remains a need for systems and methods that can be applied to facilitate delivery of treatment ultrasound energy to regions at which the blood-brain barrier is to be opened.

SUMMARY

The invention has a number of aspects. These include, without limitation:

ultrasound systems;

systems and methods for modelling a patient's tissue;

systems and methods for rapidly determining transmission parameters of treatment ultrasound beams;

systems and methods for driving ultrasound transducers;

systems and methods for rapidly varying transmission parameters of treatment ultrasound beams.

One aspect relates to a method for determining treatment values for ultrasound transmission parameters for use by an ultrasound system. The ultrasound system may comprise a plurality of ultrasound transducers to deliver treatment ultrasound energy that is focused at a target location in the brain of a subject. The method may comprise determining, based on a model of the head of the subject including the target location and surrounding tissue, intermediate values for each of a plurality of pre-treatment locations. The method may further comprise after placing the plurality of ultrasound transducers in treatment locations for delivery of ultrasound energy into the brain of the subject, determining treatment values for transmission parameters for the plurality of ultrasound transducers based at least in part on the intermediate values.

Determining the intermediate values for each of the plurality of pre-treatment locations may be performed prior to placing the plurality of ultrasound transducers in the treatment locations for delivery of ultrasound energy into the brain of the subject.

Determining the treatment values for the transmission parameters for the plurality of ultrasound transducers may comprise, for each ultrasound transducer, determining corresponding treatment values based at least in part on the intermediate values for two or more pre-treatment locations.

The method may further comprise after placing the plurality of ultrasound transducers in the treatment locations for delivery of ultrasound energy into the brain of the subject, determining the treatment locations of the plurality of ultrasound transducers. Determining the treatment values for the transmission parameters for the plurality of ultrasound transducers may be based at least in part on the determined treatment locations.

Determining the treatment locations of the plurality of ultrasound transducers may comprise determining a treatment position of a structure that supports the plurality of ultrasound transducers and determining the treatment locations of the plurality of ultrasound transducers based on known positional relationships between the structure and the plurality of ultrasound transducers.

Determining the treatment values for the transmission parameters for the plurality of ultrasound transducers may be based at least in part on one or more of the plurality of pre-treatment locations.

Determining intermediate values for each of a plurality of pre-treatment locations may comprise, for each pre-treatment location, simulating propagation of an acoustic wave from the target location to the pre-treatment location to determine an amplitude and phase of the acoustic wave at the pre-treatment location.

The intermediate values may be intermediate values for simulation parameters which, for each pre-treatment location, may comprise the amplitude and phase of the acoustic wave at the pre-treatment location.

Determining intermediate values for each of a plurality of pre-treatment locations may comprise, for each pre-treatment location, further processing the amplitude and phase of the acoustic wave at the pre-treatment location to obtain intermediate values for transmission parameters which may comprise a phase offset and amplitude scaling factor which may cause ultrasound waves originating from the pre-treatment locations to be focused at the target location.

Determining treatment values for transmission parameters for the plurality of ultrasound transducers may comprise, for each ultrasound transducer, determining corresponding treatment values. Determining corresponding treatment values may comprise interpolating intermediate values corresponding to a set of pre-treatment locations.

The set of pre-treatment locations may be based at least in part on the treatment location of the ultrasound transducer.

The set of pre-treatment locations may comprise a number of pre-treatment locations that are nearest neighbors to the treatment location of the ultrasound transducer.

Determining treatment values for transmission parameters for the plurality of ultrasound transducers may comprise, for each ultrasound transducer, determining corresponding treatment values. Determining corresponding treatment values may comprise performing a Kirchhoff Helmholtz integral (KHI).

Performing the KHI may be based at least in part on the treatment location of the ultrasound transducer, at least some of the intermediate values and at least some of the pre-treatment locations.

The KHI may have a form:

$$\breve{p}(r) = j \int \breve{p}(r') \cos \phi \ (r, r')\left(1 - \frac{j}{k(r-r')}\right)\frac{e^{-jk(r-r')}}{\lambda(r-r')}dS' \qquad (1)$$

where:

S' is a pre-treatment surface on which the pre-treatment locations are located;

r' are the pre-treatment locations on the surface S';

$\breve{p}(r')$ are complex ultrasound pressures corresponding to the intermediate values at locations r';

r are the treatment locations;

r-r' is the magnitude of the vector $\overrightarrow{r'r}$ pointing from a position r' to a position r;

cos(r,r') is a cosine of the angle $\phi(r,r')$ between a vector normal to the surface S' and the vector $\overrightarrow{r'r}$;

$\lambda$ is a wavelength of treatment ultrasound energy;

$$k = \frac{2\pi}{\lambda}$$

is a wavenumber of the treatment ultrasound energy; and $\breve{p}(r)$ is complex ultrasound pressure at the treatment location r.

The intermediate values may comprise simulation parameters. Determining corresponding treatment values may comprise determining pre-cursor treatment values which may be simulation parameters which representative of the amplitude and phase of an acoustic wave propagating from the target location to the treatment location of the corresponding transducer. Determining corresponding treatment values may also comprise converting the pre-cursor treatment values into the corresponding treatment values which comprise a phase offset and amplitude scaling factor which may cause ultrasound waves originating from the treatment locations of the plurality of ultrasound transducers to be focused at the target location.

The method may further comprise after placing the plurality of ultrasound transducers in the treatment locations for delivery of ultrasound energy into the brain of the subject, determining the treatment locations of the plurality of ultrasound transducers. Determining the treatment values for the transmission parameters for the plurality of ultrasound transducers may be based at least in part on the determined treatment locations. The method may also further comprise repeating the steps of determining the treatment locations of the plurality of ultrasound transducers and determining the treatment values for the transmission parameters for the plurality of ultrasound transducers.

Repeating the steps of determining the treatment locations of the plurality of ultrasound transducers and determining the treatment values for the transmission parameters for the plurality of ultrasound transducers may be performed while delivering treatment ultrasound energy to the subject based on the determined treatment values.

Repeating the steps of determining the treatment locations of the plurality of ultrasound transducers and determining the treatment values for the transmission parameters for the plurality of ultrasound transducers may be performed while continuously delivering treatment ultrasound energy to the subject based on the determined treatment values without interruption.

Repeating the steps of determining the treatment locations of the plurality of ultrasound transducers and determining the treatment values for the transmission parameters for the plurality of ultrasound transducers may be performed in real time within one treatment period.

Repeating the steps of determining the treatment locations of the plurality of ultrasound transducers and determining the treatment values for the transmission parameters for the plurality of ultrasound transducers may be performed in response to feedback indicating that the treatment location of one or more of the plurality of ultrasound transducers has changed.

The feedback indicating that the treatment location of one or more of the plurality of ultrasound transducers has changed may comprise feedback indicating that the treatment location of one or more of the plurality of ultrasound transducers has changed by more than a threshold amount.

The feedback indicating that the treatment location of one or more of the plurality of ultrasound transducers has changed may be provided by a proximity sensor.

The method may also comprise discontinuing delivery of treatment ultrasound energy to the subject in response to feedback indicating that the treatment location of one or more of the plurality of ultrasound transducers has changed by more than a suspension threshold amount.

The method may also comprise after discontinuing delivery of treatment ultrasound energy to the subject determining new treatment locations for the plurality of ultrasound transducers. The method may also comprise after discontinuing delivery of treatment ultrasound energy to the subject determining new treatment values for transmission parameters for the plurality of ultrasound transducers based at least in part on the intermediate values and the new treatment locations. The method may also comprise after discontinuing delivery of treatment ultrasound energy to the subject restarting delivering treatment ultrasound energy (e.g. to the target location in the brain of the subject) based on the determined new treatment values.

Determining the treatment locations of the plurality of ultrasound transducers may comprise determining a treatment position of a structure that supports the plurality of ultrasound transducers and determining the treatment locations of the plurality of ultrasound transducers based on known positional relationships between the structure and the plurality of ultrasound transducers.

The method may also comprise delivering treatment ultrasound energy (e.g. to the target location in the brain of the subject) based on the determined treatment values for the ultrasound transmission parameters for the plurality of ultrasound transducers.

Delivering treatment ultrasound energy to the subject may cause opening of a blood brain barrier.

While delivering treatment ultrasound energy to the subject based on the determined treatment values for the ultrasound transmission parameters for the plurality of ultrasound transducers, determining second treatment values for transmission parameters for a second plurality of ultrasound transducers may be based at least in part on the intermediate values. Second treatment values for the second plurality of ultrasound transducers may cause treatment ultrasound energy emitted from the second plurality of ultrasound transducers to be focused at a second target location in the brain of the subject.

The second target may be different from the target.

The second plurality of ultrasound transducers may be different than the plurality of ultrasound transducers.

The method may also comprise obtaining feedback relating to changes in the treatment locations of one or more of the plurality of ultrasound transducers. The method may also comprise adjusting the treatment values for the transmission parameters for the plurality of ultrasound transducers in response to the feedback and based at least in part on the intermediate values. The method may also comprise delivering treatment ultrasound energy to the subject based on the adjusted treatment values.

The method may also comprise continuously delivering treatment ultrasound energy to the subject based on either the determined treatment values or the adjusted treatment values without interruption.

The steps of adjusting the treatment values for the transmission parameters for the plurality of ultrasound transducers in response to the feedback delivering treatment ultrasound energy to the subject based on the adjusted treatment values may be performed in real time within one treatment period.

Obtaining the feedback relating to changes in the treatment locations of one or more of the plurality of ultrasound transducers may comprise obtaining feedback indicating that the treatment location of one or more of the plurality of ultrasound transducers has changed by more than a threshold amount.

The feedback relating to changes in the treatment locations of one or more of the plurality of ultrasound transducers may be provided by a proximity sensor.

Adjusting the treatment values for the transmission parameters for the plurality of ultrasound transducers may comprise determining updated treatment locations for one or more of the plurality of ultrasound transducers. Adjusting the treatment values for the transmission parameters for the plurality of ultrasound transducers may also comprise adjusting the treatment values for the transmission parameters for the plurality of ultrasound transducers based at least in part on the updated treatment locations.

Determining the updated treatment locations for the one or more of the plurality of ultrasound transducers may comprise determining a treatment position of a structure that supports the plurality of ultrasound transducers and determining the updated treatment locations of the plurality of ultrasound transducers based on known positional relationships between the structure and the plurality of ultrasound transducers.

The method may also comprise discontinuing delivery of treatment ultrasound energy to the subject in response to feedback indicating that the treatment location of one or more of the plurality of ultrasound transducers has changed by more than a suspension threshold amount.

The method may also comprise, after discontinuing delivery of treatment ultrasound energy to the subject, determining new treatment locations for the plurality of ultrasound transducers. The method may also comprise, after discontinuing delivery of treatment ultrasound energy to the subject, determining new treatment values for transmission parameters for the plurality of ultrasound transducers based at least in part on the intermediate values and the new treatment locations. The method may also comprise, after discontinuing delivery of treatment ultrasound energy to the subject, restarting delivering treatment ultrasound energy to the subject based on the determined new treatment values.

One aspect relates to a method for delivering treatment ultrasound energy that is focused at a target location in the brain of a subject using an ultrasound system. The ultrasound system may comprise a plurality of ultrasound transducers. The method may comprise determining treatment values for ultrasound transmission parameters for the plurality of ultrasound transducers using any method described herein. The method may also comprise delivering treatment ultrasound energy to the subject based on the determined treatment values for the ultrasound transmission parameters for the plurality of ultrasound transducers.

The method may comprise any features, combination of features or sub-combinations of features described herein.

One aspect relates to a system for determining treatment values for ultrasound transmission parameters for use by an ultrasound apparatus. The ultrasound apparatus may comprise a plurality of ultrasound transducers to deliver treatment ultrasound energy that is focused at a target location in the brain of a subject. The system may comprise a controller. The controller may be configured to determine, based on a model of the subject including the target location and surrounding tissue, intermediate values for each of a plurality of pre-treatment locations. The controller may also be configured to determine, after placing the plurality of ultrasound transducers in treatment locations for delivery of ultrasound energy into the brain of the subject, treatment values for transmission parameters for the plurality of ultrasound transducers based at least in part on the intermediate values.

The controller may be configured to perform any of the features, combination of features or sub-combinations of features described herein.

One aspect relates to an ultrasound system for delivering treatment ultrasound energy that is focused at a target location in the brain of a subject. The ultrasound system may comprise a plurality of ultrasound transducers. The ultrasound system may also comprise a controller. The controller may be configured to determine treatment values for ultrasound transmission parameters for the plurality of ultrasound transducers using any of the methods described herein. The controller may be configured to cause delivery of treatment ultrasound energy to the subject based on the determined treatment values for the ultrasound transmission parameters for the plurality of ultrasound transducers.

Another aspect of the invention provides a method for determining expected values of receive parameters of ultrasound energy focused at, and reflected from, a target location in the brain of a subject and received at a receive ultrasound transducer. The method comprises: determining, based on a model of the head of the subject including the target location and surrounding tissue, intermediate values for each of a plurality of pre-treatment locations; after placing receive ultrasound transducer in a receive location for receiving reflected ultrasound energy from the target location, determining expected values of the receive parameters for the receive ultrasound transducer based at least in part on the intermediate values.

Determining the intermediate values for each of the plurality of pre-treatment locations may be performed prior to placing the receive ultrasound transducer in the receive location.

Determining expected values of the receive parameters for the receive ultrasound transducer may comprise determining the expected values based at least in part on the intermediate values for two or more pre-treatment locations.

The method may comprise, after placing the receive ultrasound transducer in the receive location, determining the receive location of the receive ultrasound transducer. Determining the expected values of the receive parameters for the receive ultrasound transducer may be based at least in part on the determined receive location.

Determining the expected values of the receive parameters for the receive ultrasound transducer may comprise determining a treatment position of a structure that supports the receive ultrasound transducer and determining the receive location based on a known positional relationship between the structure and the receive transducer.

Determining the expected values of the receive parameters for the receive transducer may be based at least in part on one or more of the plurality of pre-treatment locations.

Determining intermediate values for each of a plurality of pre-treatment locations may comprise, for each pre-treatment location, simulating propagation of an acoustic wave from the target location to the pre-treatment location to determine an amplitude and phase of the acoustic wave at the pre-treatment location.

Determining the expected values of the receive parameters for the receive ultrasound transducer may comprise interpolating intermediate values corresponding to a set of pre-treatment locations.

The set of pre-treatment locations may be based at least in part on the receive location.

The set of pre-treatment locations may comprise a number of pre-treatment locations that are nearest neighbors to the receive location.

Determining the expected values of the receive parameters for the receive ultrasound transducer may comprise performing a Kirchhoff Helmholtz integral (KHI).

Performing the KHI may be based at least in part on the receive location, at least some of the intermediate values and at least some of the pre-treatment locations.

The KHI may have a form:

$$\breve{p}(r) = j \int \breve{p}(r') \, \cos \, \varnothing \, (r, r') \left( 1 - \frac{j}{k(r-r')} \right) \frac{e^{-jk(r-r')}}{\lambda(r-r')} dS' \tag{1}$$

where:

S' is a pre-treatment surface on which the pre-treatment locations are located;

r' are the pre-treatment locations on the surface S';

$\breve{p}(r')$ are complex ultrasound pressures corresponding to the intermediate values at locations r';

r is the receive location;

r-r' is the magnitude of the vector $\overrightarrow{r'r}$ pointing from a position r' to a position r;

cos $\varnothing(r,r')$ is a cosine of the angle $\varnothing(r,r')$ between a vector normal to the surface S' and the vector $\overrightarrow{r'r}$;

$\lambda$ is a wavelength of ultrasound energy;

$$k = \frac{2\pi}{\lambda}$$

is a wavenumber of the ultrasound energy; and $\breve{p}(r)$ is complex ultrasound pressure at the receive location r.

Another aspect of the invention provides a system for determining expected values of receive parameters of ultrasound energy focused at, and reflected from, a target location in the brain of a subject and received at a receive ultrasound transducer, the system comprising a controller configured to: determine, based on a model of the head of the subject including the target location and surrounding tissue, intermediate values for each of a plurality of pre-treatment locations; determine, after placing receive ultrasound transducer in a receive location for receiving reflected ultrasound energy from the target location, expected values of the receive parameters for the receive ultrasound transducer based at least in part on the intermediate values.

Systems described herein may comprise controllers configured (e.g. with suitable programming) to perform the features of any of the methods recited and/or described herein.

The ultrasound system may comprise any of the features, combination of features or sub-combinations of features described herein.

It is emphasized that the invention relates to all combinations of the above features, even if these are recited in different claims.

Further aspects and example embodiments are illustrated in the accompanying drawings and/or described in the following description.

BRIEF DESCRIPTION OF THE DRAWINGS

The accompanying drawings illustrate non-limiting example embodiments of the invention.

DETAILED DESCRIPTION

Figure 1:
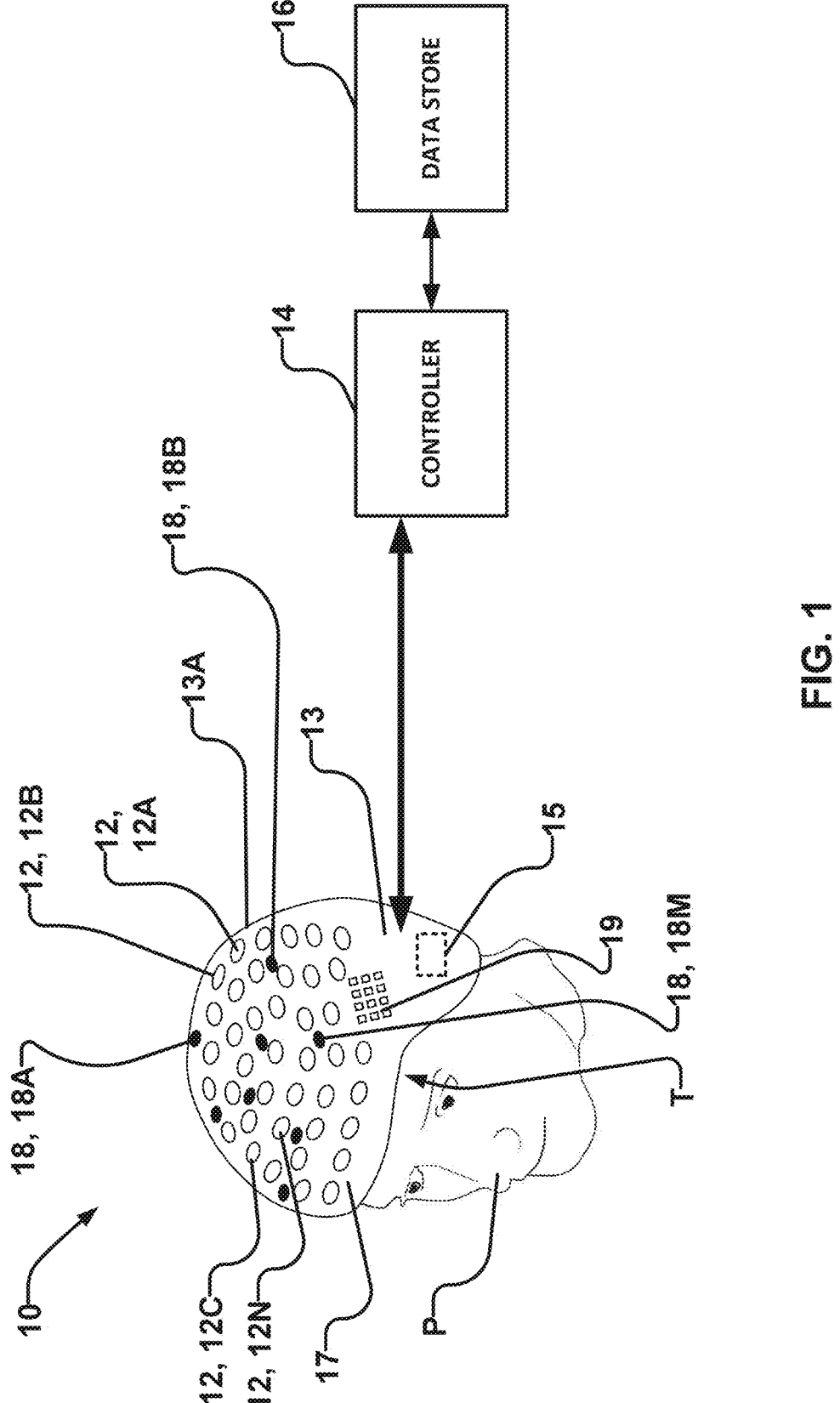
FIG. 1 is a schematic illustration of an ultrasound therapy system for delivering treatment ultrasound energy according to an example embodiment of the invention.

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive sense.

One aspect of the technology described herein provides a method for determining treatment values for transmission parameters of treatment ultrasound energy (also referred to herein as treatment ultrasound beams) to be emitted by a plurality of ultrasound transducers to provide ultrasound treatment (also referred to herein as ultrasound therapy). As used herein, ultrasound treatment or ultrasound therapy refers to ultrasound energy applied to a patient (subject) in a focused manner. Ultrasound treatment may be used, by way of non-limiting example, for opening the blood brain barrier, for ultrasound ablation, for ultrasound neuromodulation and/or the like. For each ultrasound transducer, transmission parameters for treatment ultrasound energy may comprise, without limitation, parameters which parameterize (at least in part) a complex pressure at a target (or focus) location T. For each ultrasound transducer, transmission parameters for treatment ultrasound energy may comprise without limitation, amplitude and phase (relative to a reference phase) or amplitude and time offset (relative to a reference time)). Transmission parameters may comprise some of or all of so-called beam-forming parameters, which comprise a set of parameters which are used by the plurality of ultrasound transducers to output a treatment ultrasound beam. Values of such transmission parameters used for ultrasound treatment may be referred to herein as treatment values of transmission parameters or, for brevity, treatment values. Treatment values of transmission parameters may be determined such that the treatment ultrasound beams converge at a desired focus location (e.g. a target T) and/or to provide the ultrasound treatment beams with other desired characteristics.

In some embodiments, a patient's tissue is imaged prior to treatment and the images are used to generate a model of the patient's tissue. Such imaging may comprise ultrasound imaging or any other type(s) of medical imaging technology. Such a model may comprise a physical and acoustic model, where a physical model represents the dimensions (e.g. shape and/or thickness) of layers of the tissue being modelled and an acoustic model assigns properties to each layer that parameterize or affect the sound propagation in the layer (e.g. density, sound velocity and/or the like). In some embodiments, suitable images and/or a suitable model of the patient's anatomy may be provided as an input, in which case imaging and/or construction of the model is not required.

Based on the model, a set of intermediate values may be generated prior to ultrasound treatment. The intermediate values may be determined for, or otherwise based on, a number of pre-treatment locations. Such pre-treatment locations may be comprise points in 3D space. In some embodiments, the intermediate values may comprise intermediate values of simulation parameters. For each pre-treatment location, such intermediate values of simulation parameters may comprise, for example, an amplitude and phase (or an amplitude and transmission time) of a simulated ultrasound wave propagating, through the model, from a target location T (e.g. a point in 3D space) to the pre-treatment location. In some embodiments, the intermediate values may comprise intermediate values of transmission parameters. For each pre-treatment location, such intermediate values of transmission parameters may comprise, for example, parameters which parameterize (at least in part) a complex pressure at the target location T. Such intermediate values of transmission parameters may comprise, for example, an amplitude and phase (relative to a reference phase) or amplitude and time offset (relative to a reference time), which would cause an ultrasound wave transmitted from a transducer at the pre-treatment location to be focused at a target location T.

The pre-treatment locations for which intermediate values are determined may generally comprise any locations. Without loss of generality, such pre-treatment locations may correspond to potential treatment locations for the ultrasound transducers (i.e. locations at which transducers could potentially be located for delivering ultrasound treatment). In some embodiments, pre-treatment locations may be specified, for example, by specifying a pre-treatment position of a structure that supports transducers for use in treatment. The pre-treatment position of such a structure may in turn specify pre-treatment locations based on known positional relationships between the structure and the transducers which it supports.

The plurality of ultrasound transducers may be positioned relative to the patient for treatment after the determination of intermediate values. Once the ultrasound transducers are positioned in their treatment locations, treatment values for the transmission parameters for each of the ultrasound transducers are determined based at least in part on the intermediate values (e.g. by processing one or more intermediate values to determine the treatment values for the transmission parameters for each ultrasound transducer). For each transducer, such treatment values of transmission parameters may comprise, for example, parameters which parameterize (at least in part) a complex pressure at the target location T. Such treatment values of transmission parameters may comprise, for example, an amplitude and phase (relative to a reference phase) or amplitude and time offset (relative to a reference time), which would cause an ultrasound wave transmitted from a transducer at the treatment location to be focused at a target location T.

In some embodiments, processing the intermediate values to determine treatment values for the transmission parameters may be based in part on determined or measured treatment locations of the transducers after such transducers are placed in suitable locations for treatment. Such determined or measured locations of ultrasound transducers relative to the anatomy of a particular patient, may be referred to herein as treatment locations of the ultrasound transducers or, for brevity, treatment locations. In some embodiments, treatment locations may be determined by determining a treatment position of a structure (e.g. a cap) that supports the ultrasound transducers relative to a patient and then, based on known relationships of the locations of the transducers to the transducer-supporting structure, determining the treatment locations of the ultrasound transducers. In some embodiments, treatment locations may be determined by determining treatment locations of a subset of the transducers and then, based on known relationships of the locations of the transducers with one another, determining the treatment locations of the remaining ultrasound transducers.

In some embodiments, processing the intermediate values to determine treatment values for the transmission parameters may be based in part on the pre-treatment locations (for which the intermediate values are determined). In some embodiments, determining the treatment values for the transmission parameters for the transducers may involve interpolating between intermediate values based on the determined or measured treatment locations of the transducers and the pre-treatment locations. In some embodiments, determining the treatment values for the transmission parameters for each of the transducers may involve suitable application of an analytical computation, such as, for example, a Kirchhoff Helmholtz integral (KHI). Such an analytical computation may be based, for example, on: the intermediate values, the determined or measured treatment locations of the ultrasound transducer and the pre-treatment locations. In some embodiments, where the intermediate values are simulation parameters, processing the intermediate values to determine treatment values for the transmission parameters may comprise a two-step process of processing the intermediate values to determine pre-cursor treatment values (which may also be simulation parameters) and then converting the simulation parameters to transmission parameters to obtain the treatment values for transmission parameters.

FIG. 1 is a schematic illustration showing an example ultrasound system 10 which may be used in accordance with (e.g. to the implement the methods of) various embodiments of the invention. System 10 comprises a plurality of transmit ultrasound transducers 12 (referred to herein for brevity as ultrasound transducers 12 or transducers 12) which may be used to deliver focused ultrasound beams to a desired target T (also referred to herein as a focus location T) within the head of a patient P and which may open the blood brain barrier in a corresponding region within the head of patient P. Typically, controller 14 sets treatment values for various transmission parameters of the ultrasound waves to be emitted by each of transmit transducers 12 to cause ultrasound waves emitted by transducers 12 to converge at (be focused at) the target T. By way of non-limiting example, such transmission parameters may include the frequency, pulse length, amplitude, phase (relative to a reference phase), time offset (relative to a reference time) and/or the like. In one example embodiment, the plurality of ultrasound transducers 12 may be located on a head-covering (e.g. a cap) 13A to thereby facilitate positioning of transducers 12 around the head of patient P. Energy from the ultrasound beams may, for example, be used to open the blood-brain barrier of patient P. Opening up the blood-brain barrier may permit diffusion of molecules (e.g. drugs) into brain tissue to, for example, treat cancerous tumors. Additionally, or alternatively, opening up the blood-brain barrier may permit diffusion of molecules and/or cells out of brain tissue into the blood stream to detect one or more properties of the brain tissue (e.g. detect the presence of cancerous tumors, biomarkers, etc.). Energy from the treatment ultrasound beams may be used for other kinds of ultrasound therapy on patient P (e.g. ultrasound ablation, ultrasound neuromodulation and/or the like).

As shown in FIG. 1, ultrasound transducers 12A, 12B, 12C, . . . , 12N (collectively, ultrasound transducers 12) may be distributed around the head of patient P. In one example configuration, ultrasound transducers 12 comprise transducer elements having a diameter of about 7 mm. Ultrasound transducers 12 may be configured to operate at about 220 kHz. Ultrasound beams emitted by transducers 12 may have an acoustic pressure in a region in which the ultrasound beams impinge in an amplitude range from about 0.2 MPa to about 1 MPa.

Ultrasound transducers 12 may be supported by a transducer-supporting structure 13, of which cap 13A is an example. Structure 13 may extend between and support adjacent ones of ultrasound transducers 12. Structure 13 may support transducers 12 at fixed or known locations relative to structure 13, relative to one or more identifiable features of structure 13 and/or relative to one another. In some embodiments, transducer-supporting structure 13 supports plural arrays of transducers 12 which may be selectively activated as part of any ultrasound treatment plan. In some embodiments, any subset of transducers 12 can be selectively activated as part of any ultrasound treatment plan. In some embodiments, cap 13A can be provided according to the cap described in the Patent Cooperation Treaty (PCT) application published under WO2021/154730 which is hereby incorporated herein by reference. In some embodiments, transducer-supporting structure 13 is provided in the form of a cap 13A which may be placed at least partially over patient P's head. Suitable portion(s) of structure 13 (e.g. the cap 13A) may be elastomeric, so that such portion(s) may be stretched to fit over the head of patient P and the forces that tend to restore such portion(s) of structure 13 to their non-deformed state may tend to keep structure 13 (and transducers 12) in place on the head of patient P. For example, such restorative forces may prevent (or mitigate) structure 13 from slipping relative to the head of patient P and may thereby maintain, to the extent possible, the treatment locations transducers 12 relative to the head of patient P after structure 13 (e.g. cap 13A) is placed on the head of patient P. The elastomeric portions of structure 13 are not required. In other embodiments, structure 13 may be rigid. In general, structure 13 may be maintained in place relative to the anatomy (head) of patient P using any suitable technique.

In some embodiments, the transducer-supporting portion(s) 17 of structure 13 (e.g. cap 13A) are rigid. Positions of individual transducers 12 may be fixed relative to one another, relative to structure 13 and/or relative to one or more identifiable features of structure 13. In such cases, by knowing (e.g. by measurement or otherwise) a position of structure 13, a transducer 12 and/or one or more other identifiable features of structure 13, locations of the other ones of transducers 12 may be determined based on known positional relationships of transducers 12 relative to structure 13 and/or relative to one another.

Controller 14 is configured to control transducers 12 to emit ultrasound beams with desired treatment values for their corresponding transmission parameters. For example, controller 14 may set an amplitude, phase (e.g. relative phase or relative time offset), frequency, pulse length and/or other parameters of the ultrasound wave to be emitted by each transducer 12, such that the ultrasound waves emitted by transducers 12 converge at (i.e. are focused on) an intended target (focal location) T. As described elsewhere herein, treatment ultrasound energy focused at target T may cause a corresponding region (e.g. a volume) of the blood-brain barrier to be opened. Because the precise location of transducers 12 (relative to the target T) may vary depending on the manner in which structure 13 (e.g. cap 13A) is applied to the head of patient P, it can be desirable to determine treatment values of the transmission parameters for transducers 12 after the application of structure 13 to patient P (e.g. after cap 13A is placed on the head of patient P). The locations of transducers 12 relative to the anatomy (e.g. head) of patient P after application of structure 13 to patient P may be referred to herein as the treatment locations of transducers 12. The values of the ultrasound transmission parameters for each of transducers 12 used for treatment of patient P may be referred to herein as treatment values of the ultrasound transmission parameters or, for brevity, treatment values. Determining treatment values of the transmission parameters for each of transducers 12 may be computationally expensive, especially if there are a large number of transducers 12 (e.g. more than 20 transducers, more than 100 transducers, more than 500 transducers, more than 1000 transducers, etc.). In some embodiments, transducers 12 are divided into a plurality of sets (or arrays or modules) of transducers 12—see, for example, FIG. 8 and the related discussion below. Each set of transducers 12 may be independently controlled to emit ultrasound waves (e.g. successively and/or simultaneously), which may be focused at a different target T (or targets) than the other set(s) of transducers 12.

Because the precise treatment locations of transducers 12 relative to the target (focus location) T may vary depending on the manner in which structure 13 (e.g. cap 13A) is applied to the head of patient P, determining treatment values of the transmission parameters for transducers 12 is typically performed after the application of structure 13 to patient P. There is a general desire to minimize, reduce and/or keep to an acceptable level, the time that it takes to determine treatment values of the transmission parameters after the application of structure 13 to patient P (e.g. after cap 13A is placed on the head of patient P) for a number of reasons. By way of non-limiting example, reasons to minimize, reduce and/or keep to an acceptable level, the time that it takes to determine treatment values after the application of structure 13 to patient P may include: taking more time to determine treatment values of the transmission parameters means more likelihood of relative movement between transducers 12 and/or structure 13 and the head of patient P; taking more time to determine treatment values of the transmission parameters means more professional time of medical practitioners is consumed to perform treatments; taking more time to determine treatment values of the transmission parameters means more treatment time (i.e. time during which a particular patient P occupies expensive ultrasound equipment or is subjected to the experience of being treated), and/or the like.

Without being limited to a particular theory of operation, the inventors have discovered that significant amounts of time and/or computational resources, particularly time and/or computational resources after structure 13 is applied to (e.g. cap 13A is put on) the head of patient P and ultrasound system 10 is otherwise ready for use to apply ultrasound treatment, may be saved by: pre-determining intermediate values based on pre-treatment locations and a model of the head of patient P before structure 13 is applied to (e.g. cap 13A is put on) the head of patient P; and then, once structure 13 is applied to (e.g. cap 13A is put on) the head of patient P, determining the treatment values of ultrasound transmission parameters to be used for transducers 12 by processing the intermediate values. In some embodiments, the intermediate values are processed to determine treatment values for the transmission parameters. In some embodiments, such processing may be based in part on determined or measured treatment locations of the transducers 12. In some embodiments, such processing may be based in part on the pre-treatment locations (for which the intermediate values are determined).

Processing the intermediate values to determine the treatment values for the ultrasound transmission parameters may be based in part on the treatment locations of transducers 12 after structure 13 is applied to (e.g. cap 13A is put on) the head of patient P. In some embodiments, processing the intermediate values to determine treatment values for the ultrasound transmission parameters may be based in part on the pre-treatment locations (for which the intermediate values are determined). In some embodiments, determining treatment values for the transmission parameters to be used for transducers 12 for ultrasound treatment may comprise interpolating intermediate values associated with pre-treatment locations, wherein such interpolation is based on treatment locations of transducers 12 measured or otherwise determined after structure 13 is applied to (e.g. cap 13A is put on) the head of patient P. In some embodiments, determining treatment values for the transmission parameters to be used for transducers 12 for ultrasound treatment may be based on suitable application of an analytical computation, such as, for example, a Kirchhoff Helmholtz integral (KHI). Such an analytical computation may be based, for example, on: the intermediate values, the treatment locations of transducers 12 measured or otherwise determined after structure 13 is applied to (e.g. cap 13A is put on) the head of patient P and the pre-treatment locations.

In some embodiments, treatment locations of the ultrasound transducers 12 may be determined by determining a position of structure 13 relative to patient P and then, based on known relationships of the positions of transducers 12 to structure 13, determining the treatment locations of the ultrasound transducers 12. In some embodiments, treatment locations of the ultrasound transducers 12 may be determined by determining treatment locations of a subset of the transducers 12 and then, based on known relationships of the locations of the transducers 12 with one another, determining the treatment locations of the remaining ultrasound transducers 12.

Ultrasound system 10 may comprise one or more location sensors 15 which may be configured to determine treatment locations of transducers 12 (e.g. the locations of transducers 12 relative to the anatomy/head of patient P after structure 13 is applied to (e.g. placement of cap 13A on) the head of patient P). In some embodiments, system 10 comprises a location sensor 15 for each transducer 12. In some embodiments, system 10 comprises a location sensor 15 for individual sets (arrays or modules) of transducers 12 (e.g. treatment locations of the transducers 12 within a set may be determined based on known relationships of the transducers 12 relative to one another). In some embodiments, system 10 comprises a single location sensor 15 (e.g. treatment locations of transducers 12 may be determined based on known relationships of transducers 12 relative to one another or relative to the treatment position of structure 13). In some embodiments, location sensor 15 may comprise one or more sensors for determining a location of one or more identifiable features (e.g. markers or the like) of structure 13 relative to the anatomy of patient P, after which the treatment locations of transducers 12 may be determined based on known relationships between transducers 12 and structure 13 and/or known relationships between the transducers 12 and the one or more identifiable features. In some embodiments, sensor 15 may comprise an MRI imaging system, a stereoscopic imaging system and/or the like, which may be able to determine the treatment position of structure 13, the treatment position(s) of identifiable feature(s) of structure 13 and/or the treatment locations of transducers 12. Sensors 15 may be located on structure 13, structure 13 and patient P and/or otherwise suitable located relative to patient P for detecting relative motion between structure 13 and patient P.

Sensors 15 may, for example, comprise one or more of:
  a plurality of receive ultrasound transducers which may be interspersed with transducers 12 and supported in structure 13;
  a plurality of imaging ultrasound transducers 19 specifically configured for imaging;
  a plurality of accelerometers (e.g. coupled to a transducer 12, embedded within structure 13, etc.);
  a marker tracking imaging-based system (e.g. an MRI imaging system, a stereoscopic imaging system and/or the like), where a plurality of markers or other identifiable features are positioned on transducer(s) 12 and/or structure 13 and are tracked by the imaging system;

an electromagnetic based location tracking system which may track locations of one or more identifiable features positioned on transducer(s) 12 and/or structure 13 and/or patient P. For example, optical based sensors may detect markers which may be placed on transducers 12, structure 13 and/or patient P;

etc.

In some embodiments, treatment locations of transducers 12 may at least partially be determined by registering an image (or images) of patient P captured with ultrasound transducers 12 and/or imaging ultrasound transducers 19 against prior captured images of patient P (e.g. CT image, MRI image data, prior acquired ultrasound images). A non-limiting example of such a process is described in the PCT application published under publication No. WO2018/ 026738, which is hereby incorporated herein by reference.

In some embodiments, a position of structure 13 (e.g. cap 13A) relative to patient P is determined (e.g. by one or more sensor(s) 15 or otherwise). Based on known positional relationships of transducers 12 to structure 13, treatment locations of transducers 12 may be determined based on the determined position of structure 13.

In some embodiments, ultrasound system 10 may be configured to image the head of patient P once structure 13 is applied to the head of patient P. Based on imaged anatomical features of the head of patient P (e.g. the Circle of Willis, etc.), the position of structure 13 may be registered relative to the head of patient P. For example, ultrasound system 10 may comprise at least one imaging ultrasound transducer 19 configured to image the head of patient P. The location of the at least one imaging transducer 19 relative to structure 13 and/or to treatment transducers 12 may be known. By registering imaged anatomical features of the head of patient P relative to the at least one imaging transducer 19, a position of structure 13 relative to the head of patient P may be determined. As described elsewhere herein, treatment locations of transducers 12 may then be determined based on known positional relationships of transducers 12 to structure 13. In some embodiments, a position of structure 13 (or cap 13A) is determined as described in PCT publication No. WO2018/026738.

Based on determined treatment locations of transducers 12 or a determined position of structure 13 (or cap 13A) relative to the head of patient P (from which treatment locations of transducers 12 may be determined), controller 14 may determine appropriate treatment values of the transmission parameters for ultrasound beams emitted by transducers 12 to converge at target (focus location) T. In some embodiments, controller 14 retrieves the intermediate values from a data store 16 and generates the treatment values of the transmission parameters for transducers 12 based on the intermediate values. In some embodiments, the intermediate values are stored in a look-up table or similar data structure.

Figure 2:
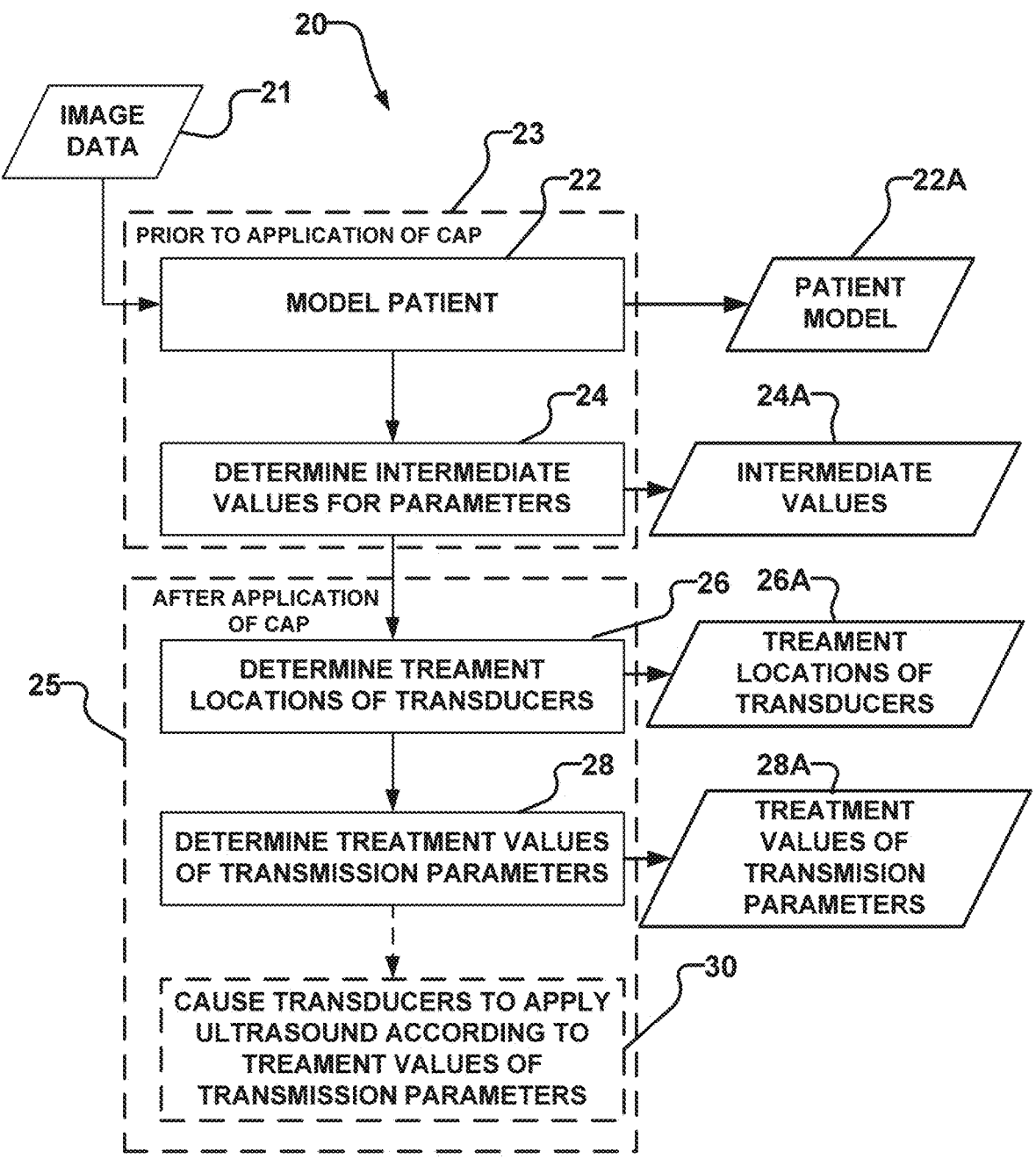
FIG. 2 is a block diagram illustrating a method according to an example embodiment of the invention.

FIG. 2 is a block diagram which illustrates an example method 20 for determining treatment values 28A for transmission parameters of ultrasound beams to be emitted by ultrasound transducers 12. Method 20 may optionally be divided into two parts (shown in dashed outline in FIG. 2) which include: part 23 which occurs prior to the application of structure 13 to the head of patient P; and part 25 which occurs after the application of structure 13 to the head of patient P. The division of method 20 into parts 23 and 25 is optional and part 23 or some steps of part 23 could additionally or alternatively be performed after the application of structure 13 to the head of patient P.

Block 22 involves generating a simulation model 22A of patient P (a patient model 22A, which may be used for simulating the propagation of ultrasound waves in patient P. For example, the head (e.g. skull, locations of target T, brain tissue, etc.) of patient P may be modelled in patient model 22A. In some embodiments, patient model 22A comprises a physical and acoustic model of patient P (i.e. a model which both physically and acoustically models the head of patient P) where a physical model represents the dimensions (e.g. shape and/or thickness) of layers of the object being modelled and an acoustic model assigns properties to each layer that include or affect the sound propagation in the layer (e.g. density, sound velocity and/or the like). Image data 21 previously collected from patient P may be used in block 22 to generate patient model 22A. Preferably, image data 21 used to generate patient model 22A is relatively recent (e.g. taken within 2 days, 1 week, 1 month, etc. of patient P's treatment). In some embodiments, image data 21 comprises CT data and/or MRI data. In some embodiments, block 22 may involve using image data 21 to generate a 3D model 22A of the head (e.g. skull, locations of the target T, brain tissue, etc.) of patient P. In some embodiments, image data 21 itself may comprise 3D image data, which may be used in block 22 to construct a 3D model 22A of the head of patient P. In some embodiments, method 20 comprises performing the imaging process to procure image data 21. The block 22 patient model 22A may comprise a modelled 3D location or point corresponding to the target T in the particular patient P. One or more target(s) T may be identified in model 22A or identified in image data 21 and transferred to model 22A. In general, image data 21 may comprise any suitable type of image data 21 that can be used to construct any suitable patient model 22A which is capable of supporting the simulations described herein. In general, patient model 22A may comprise any suitable model that is capable of supporting the simulations described herein and block 22 may comprise any suitable technique for construction such a model. In some embodiments, model 22A is provided as an input, in which case block 22 is not required as a part of method 20.

Block 24 comprises determining a plurality of intermediate values 24A based in part on patient model 22A. Intermediate values 24A may be determined for, or otherwise based on, a number of pre-treatment locations 31 (see discussion of FIGS. 3 and 5 below). Such pre-treatment locations 31 may comprise points in 3D space. Pre-treatment locations 31 may correspond to potential locations for transducers 12, although this is not generally necessary. A set of intermediate values 24A may be determined in block 24 for each pre-treatment location 31. Intermediate values 24A may be generated (in block 24) by simulating propagation of ultrasound waves through patient model 22A (e.g. from a focus location (e.g. a target T) in patient model 22A through to pre-treatment locations 31 on an exterior of the head of patient P). In typical examples, the frequency of the simulated ultrasound wave used to determine intermediate values 24A in block 24 is assumed to be the same frequency of the treatment ultrasound energy proposed to be used for transducers 12 during treatment. In some embodiments, intermediate values 24A are generated for a plurality of different targets (focus locations) T in patient model 22A. Intermediate values 24A may be different for different ones of the targets T. Intermediate values 24A may be stored (e.g. in a look up table) for subsequent use.

In some embodiments, intermediate values 24A may comprise intermediate values 24A of simulation parameters. For each pre-treatment location 31, such simulation parameters may comprise, for example, an amplitude and phase of a simulated ultrasound wave propagating, through patient model 22A, from the target location T to the pre-treatment location 31.

In some embodiments, intermediate values 24A may comprise intermediate values 24A of transmission parameters. For each pre-treatment location 31, such transmission parameters may comprise, for example, parameters which parameterize or define (at least in part) a complex pressure at the target location T. For each pre-treatment location 31, such transmission parameters may comprise amplitude and phase (relative to a reference phase) or amplitude and time offset (relative to a reference time). Such transmission parameters may parameterize or otherwise define (at least in part) complex pressures which would cause ultrasound waves transmitted from transducers located at the pre-treatment locations 31 to be focused at the target location T. In some embodiments, such transmission parameters may comprise, for each pre-treatment location 31, a phase (or time) offset transmission parameter which specifies a phase (or time) offset relative to that of a reference pre-treatment location 31 and an amplitude scaling transmission parameter which specifies an amplitude scaling factor relative to that of a reference pre-treatment location 31.

Intermediate values 24A for transmission parameters may be determined by further processing intermediate values 24A for simulation parameters (e.g. simulation phases and simulation amplitudes) obtained as discussed above. For example, simulation phases obtained by simulating the propagation of an ultrasound wave from target T to each pre-treatment location 31 can be: negated and then offset by subtracting the negated simulation phase of a reference pre-treatment location 31 to obtain intermediate values 24A for phase offset transmission parameters. A similar process may be used to obtain intermediate values 24A for time offset transmission parameters. By way of non-limiting example, simulation amplitudes obtained by simulating the propagation of an ultrasound wave from target T to each pre-treatment location 31 can be scaled by a corresponding scaling factor to make the amplitude for each pre-treatment location 31 match the amplitude at a reference pre-treatment location 31 and such scaling factors can be used as intermediate values 24A for amplitude scaling transmission parameters. Other techniques may be used to convert amplitude simulation parameters to amplitude transmission parameters. In other embodiments, other suitable techniques may be used to convert intermediate values 24A for simulation parameters into intermediate values 24A for transmission parameters, where such transmission parameters parameterize or define (at least in part) a complex pressure at the target location T which may be transmitted by an ultrasound transducer.

As described in more detail below, intermediate values 24A can be used (e.g. in part 25 after the application of structure 13 to the head of patient P) as a basis to rapidly generate treatment values 28A of transmission parameters for transducers 12.

After application of structure 13 (e.g. cap 13A) to patient P, method 20 proceeds to block 26 which involves determining treatment locations 26A of transducers 12. As discussed above, treatment locations 26A of transducers 12 comprise the locations of ultrasound transducers 12 relative to the anatomy of a particular patient P. Treatment locations 26A may be specified as points in 3D space.

In some embodiments, as described elsewhere herein, transducers 12 are supported and fixed relative to one another by a rigid structure 13 (e.g. a rigid version of cap

13A or a cap with a rigid transducer-supporting portion 17) or any other version of structure 13 which fixes the locations of transducers 12 relative to structure 13 and/or relative to one another. Block 26 may involve determining the position of structure 13 relative to the anatomy of patient P (the treatment position of structure 13). The treatment position of structure 13 relative to patient P may be determined, for example, by registering structure 13 relative to anatomical structure(s) of patient P (e.g. the Circle of Willis). Such a technique is described, for example, in the PCT application published under publication No. WO2018026738. The treatment position of structure 13 relative to patient P may be determined in any one or more of up to 6 degrees of freedom (e.g. any of 3 translation and 3 orientation degrees of freedom). Once the treatment position of structure 13 is determined, treatment locations 26A of individual transducers 12 may be determined based on the known positions of transducers 12 relative to structure 13.

As another example, treatment locations 26A of transducers 12 may be determined (measured) by processing data from sensor(s) 15 as described elsewhere herein. Additionally, or alternatively, treatment locations 26A of transducers 12 may at least partially be determined (measured) in block 26 by registering captured images against prior captured images, as described elsewhere herein.

In still other embodiments, treatment locations 26A of transducers 12 may be determined by any suitable technique known now or developed in the future.

It will be appreciated that, for accurate measurement of treatment locations 26A of transducers 12 using currently known techniques, it is desirable for the cap 13A to be located on the head of patient P (e.g. for structure 13 to be applied to patient P). Consequently, block 26 is shown in FIG. 2 as being within part 25 of method 20, after the application of structure 13 to the head of patient P.

After determining treatment locations 26A of transducers 12, method 20 then proceeds to block 28. Block 28 involves processing the block 24 intermediate values 24A for a particular target (focus location) T or targets T to determine treatment values 28A for transmission parameters for ultrasound beams to be emitted by transducers 12. Block 28 may be performed in part 25 of method 20 (i.e. after structure 13 (e.g. cap 13A) is applied to the head of patient P). In some embodiments, the block 28 processing of intermediate values 24A to determine treatment values 28A may be based in part on the block 26 treatment locations 26A of transducers 12 relative to patient P. In some embodiments, the block 28 processing of intermediate values 24A to determine treatment values 28A may be based in part on pre-treatment locations 31 (for which intermediate values 24A are obtained). In some embodiments, determining treatment values 28A may involve interpolating between intermediate values 24A based on treatment locations 26A of transducers 12 and pre-treatment locations 31. In some embodiments, determining treatment values 28A may involve suitable application of an analytical computation, such as, for example, a Kirchhoff Helmholtz integral (KHI). Such an analytical computation may be based, for example, on: intermediate values 24A, treatment locations 26A of transducer 12 and pre-treatment locations 31.

In some embodiments, where intermediate values 24A are simulation parameters, processing intermediate values 24A to determine treatment values 28A for the transmission parameters in block 28 may comprise a two-step process of processing intermediate values 24A to determine pre-cursor treatment values (which may also be simulation parameters) and then converting the pre-cursor treatment values for simulation parameters to transmission parameters to obtain the treatment values 28A for transmission parameters. In this sense, pre-cursor treatment values may be considered to be, or may comprise, for each transducer 12, an estimate of the simulation parameters (e.g. an amplitude and phase) of an acoustic wave propagating (e.g. through model 22A) from the target location T to the treatment location 26A of the transducer 12. Similarly, converting these pre-cursor treatment values into corresponding treatment values for transmission parameters may be considered to be, or may comprise, a phase (or time) offset and amplitude scaling factor which would cause ultrasound waves originating from the treatment locations of the plurality of ultrasound transducers to be focused at the target location. The conversion of pre-cursor treatment values for simulation parameters to transmission parameters to obtain the treatment values 28A for transmission parameters may be done after interpolation and/or analytical computation (which may be done in the space of simulation parameters). The conversion of pre-cursor treatment values for simulation parameters to transmission parameters to obtain the treatment values 28A for transmission parameters may be the last step of block 28. The conversion of pre-cursor treatment values for simulation parameters to transmission parameters to obtain the treatment values 28A for transmission parameters may, in some embodiments, be substantially similar to the conversion of intermediate values 24A from simulation parameters to transmission parameters as discussed herein in connection with block 24, except that treatment locations 26A may be used in the place of intermediate locations 31.

In some embodiments, blocks 26 and 28 may be repeated (e.g. the block 28 treatment values 28A for transmission parameters may be dynamically varied or controlled in real time) if a block 26 treatment location 26A of at least one transducer 12 (or a location of structure 13 generally) is varied or varies by more than a threshold amount from a first determination of treatment locations 26A (e.g. by more than $\frac{1}{16}^{th}$, $\frac{1}{8}^{th}$, $\frac{1}{4}^{th}$, etc. of the wavelength of the treatment ultrasound beam). This real time control of treatment values 28A is described, for example, in connection with FIG. 7 below, where treatment values 28A are controlled in real time based on feedback relating to (e.g. updates to) treatment locations 26A.

In some cases, it is desirable to open the blood-brain barrier (or to provide other therapeutic effects, such as ultrasound ablation, ultrasound neuromodulation and/or the like) in region(s) or volume(s) of patient P which involve focusing treatment ultrasound at a plurality of M target locations $T_1, T_2, \ldots T_M$. In some such cases, the block 28 treatment values 28A for transmission parameters for different target locations $T_1, T_2, \ldots$ may be determined sequentially or simultaneously.

In some embodiments, method 20 involves the optional block 30 step of causing transducers 12 to apply treatment ultrasound energy to patient P using the block 28 treatment values 28A for the transmission parameters of transducers 12. In some embodiments involving the block 30 application of treatment ultrasound energy to patient P and where there are a plurality of M target locations $T_1, T_2, \ldots T_M$, ultrasound energy is delivered (e.g. in block 30) for a first target T, while the steps of block 28 (and optionally block 26) may be used to determine treatment values 28A for transmission parameters of transducers 12 for a subsequent target. That is, treatment values 28A for one or more subsequent targets are being determined (according to the procedures of block 28 described herein) while treatment ultrasound is being delivered to a first target. In some embodiments, the sets of transducers 12 used for each target $T_1, T_2, \ldots T_M$ may be, but need not be, the same. If the transducers 12 used for different targets $T_1, T_2, \ldots T_M$ are not the same, then block 26 may be used to determine treatment locations of the set of transducers 12 involved for each target $T_1, T_2, \ldots T_M$. In some embodiments, a first iteration of block 26 may determine positions for all of the transducers 12 which may be used for different targets $T_1, T_2, \ldots$, in which case block 26 need not be performed separately for the set of transducers 12 involved for each target $T_1, T_2, \ldots T_M$.

Additional details are now provided in respect of particular embodiments of method 20.

Figure 3:
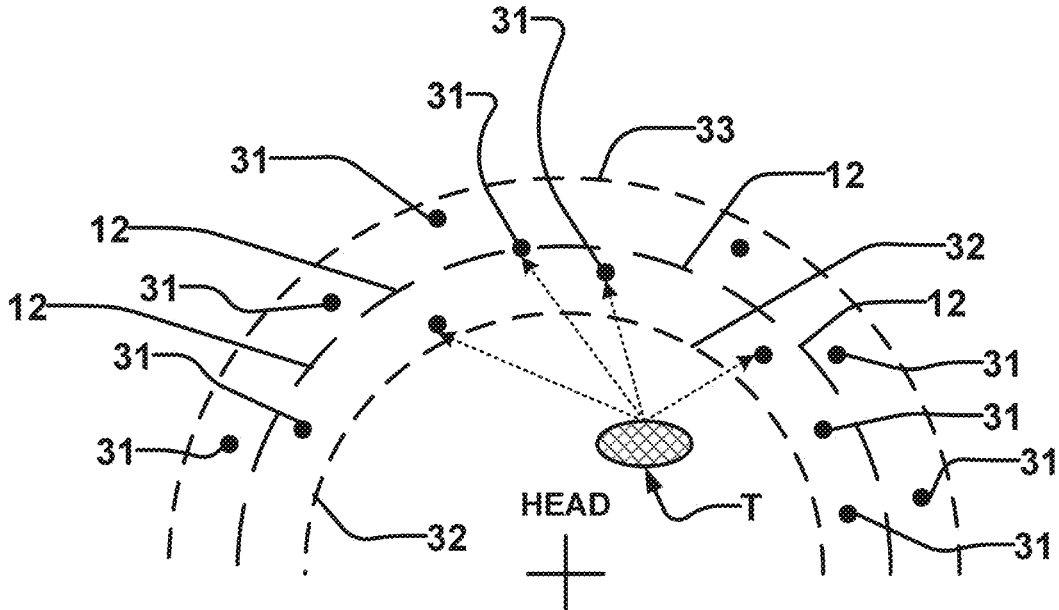
FIG. 3 is a schematic illustration of pre-treatment locations at which intermediate values may be determined according to an example embodiment of the invention.

In some embodiments, intermediate values 24A may be generated in block 24 by determining an acoustic path for the ultrasound waves from a target point or location T through patient model 22A to each of a plurality of pre-treatment locations 31. Pre-treatment locations 31 may correspond to the centers (or some other particular locations—e.g. particular corners) of small volumes (voxels). That is, there may be a pre-treatment location 31 for each voxel in a region of space. For example, as shown in FIG. 3, transducers 12 may be ultimately located between an inner boundary 32 (which may correspond to the outer surface of the skull of patient P) and a configurable outer boundary 33. While FIG. 3 is a schematic cross-section, it will be appreciated that the volume between inner boundary 32 and outer boundary 33 may be discretized into voxels with one pre-treatment location 31 corresponding to each voxel and located at a particular location (e.g. a center or corner) of the corresponding voxel. It will be further appreciated that the dimensionality of such voxels is a configurable parameter. In some embodiments, pre-treatment locations 31 are specified as points in 3D space.

In some embodiments, pre-treatment locations 31 may be specified by a pre-treatment position (in any of up to six degrees of freedom) of structure 13 (or pre-treatment locations of a subset of transducers 12). For example, where structure 13 supports transducers 12 in a known relationship relative to structure 13 and/or to one another, pre-treatment locations 31 may be specified by the known locations of transducers 12 relative to a pre-treatment position of structure 13 and/or relative to pre-treatment locations of a subset of transducers 12.

For each pre-treatment location 31, intermediate values 24A may be determined as discussed above by simulating acoustic paths between target (focus location) T and the pre-treatment location 31. Acoustic paths may be simulated using a model of the head of patient P (e.g. patient model 22A) from the modelled target location T to pre-treatment locations 31. Simulating such acoustic paths may comprise placing a virtual point ultrasound transmitter at the modelled target location T and using a finite difference time domain (FDTD) solver or any other suitable simulation technique (e.g. based on model 22A) to simulate the propagation of ultrasound waves from target T to the pre-treatment locations 31. As discussed above, in some embodiments, intermediate values 24A may comprise intermediate values 24A of simulation parameters (simulated from target T to pre-treatment locations 31) and, in some embodiments, intermediate values 24A comprise may comprise intermediate values 24A of transmission parameters (parameters that would cause an ultrasound beam originating from pre-treatment locations 31 to be focused at target T). In either case, determining intermediate values 24A in block 24 may comprise simulating acoustic propagation using a FDTD solver or other suitable simulation technique. Such FDTD solver simulations can be complex, computationally expensive and correspondingly time consuming, for example, because of the various anatomical and/or other layers through which sound waves propagate between target T and pre-treatment locations 31. It will be appreciated, however, that simulating acoustic paths in this manner (using FDTD solver-based simulations or other simulations based on model 22A) to determine intermediate values 24A may be performed in part 23 of method 20, before structure 13 is applied to the head of patient P (e.g. before cap 13A is put on the head of patient P).

In part 25 of method 20, once structure 13 is applied to the head of patient P (e.g. after cap 13A is put on the head of patient P), the treatment locations 26A of transducers 12 are determined in block 26. As discussed above, treatment locations 26A of transducers 12 (which may be specified as points in 3D space) may be determined using any suitable technique.

In some embodiments, once treatment locations 26A are determined in block 26, treatment values 28A of transmission parameters for the treatment locations 26A of transducers 12 may be determined in block 28 for each transducer 12. For each transducer 12 (or each treatment location 26A), treatment values 28A may be determined based on intermediate values 24A corresponding to a set of "nearest neighbor" pre-treatment locations 31 (e.g. for each transducer 12, a set of pre-treatment locations 31 that are proximate to the treatment location 26A of the transducer 12). In some embodiments, the set of nearest neighbors comprises eight (or any other suitable number of) nearest neighbors of pre-treatment locations 31 nearest to an actual treatment location 26A for a transducer 12). In some embodiments, the number of nearest neighbor pre-treatment locations 31 involved in determining treatment values 28A for a particular transducer 12 may be a configurable parameter of method 20. In some embodiments, a distance threshold within which pre-treatment locations 31 may be considered to be nearest neighbors involved in determining treatment values 28A for a particular transducer 12 may be a configurable parameter of method 20.

In some embodiments, determining treatment values 28A of transmission parameters based on intermediate values 24A comprises, for each transducer 12, interpolating the intermediate values 24A corresponding to a plurality of pre-treatment locations 31 that are nearest neighbors to the treatment location 26A for that transducer 12. Such interpolation may comprise linear interpolation, multi-variate interpolation, spline interpolation and/or any other suitable interpolation technique. For a particular transducer 12 measured (or otherwise determined) to be at a particular treatment location 26A, the interpolation weights associated with each nearest neighbor pre-treatment locations 31 may be inversely correlated (e.g. inversely proportional) to a distance between the nearest neighbor pre-treatment location 31 and the treatment location 26A of the transducer 12. In some embodiments, rather than interpolation, determining the treatment values 28A of the transmission parameters for a particular transducer 12 may comprise selecting the treatment values 28A for a particular transducer 12 to correspond to the intermediate values 24A for a single nearest neighbor (e.g. the closest) pre-treatment location 31. This technique may be appropriate, for example, where the density of pre-treatment locations 31 is dense (e.g. the discretization interval of pre-treatment locations 31 is small).

As discussed above, intermediate values 24A may comprise intermediate values 24A for simulation parameters (simulated from target T to pre-treatment locations 31) or intermediate values for transmission parameters (parameters that would cause an ultrasound beam originating from pre-treatment locations 31 to be focused at target T). Where intermediate values 24A comprise intermediate values 24A for transmission parameters, treatment values 28A may be obtained directly from the interpolation of intermediate values 24A. However, where intermediate values 24A comprise intermediate values 24A for simulation parameters, then the interpolation of intermediate values 24A in block 28 will yield interpolated values of simulation parameters (referred to herein as pre-cursor treatment values) for each transducer 12 at each treatment location 26A. In such embodiments, block 28 may comprise the additional step of converting the interpolated values of the simulation parameters (pre-cursor treatment values) into treatment values 28A of transmission parameters. This block 28 conversion of interpolated values of simulation parameters (pre-cursor treatment values) into treatment values 28A of transmission parameters may be similar to the conversion of intermediate values 24A of simulation parameters into intermediate values 24A of transmission parameters discussed above in connection with block 24, except that treatment locations 26A may be used in the place of pre-treatment locations 31.

In some embodiments, intermediate values 24A are computed in block 24 for one or more pre-treatment positions of structure 13 (or cap 13A) relative to patient P. For example, intermediate values 24A may be computed for pre-treatment locations 31 that correspond to the location of each transducer 12 based on a pre-treatment position of structure 13 in up to 6 degrees of freedom and the positional relationship of the transducer 12 to structure 13. That is, each pre-treatment position of structure 13 may specify a set of pre-treatment locations 31 based on the known positional relationships between transducers 12 and structure 13.

Once structure 13 (or cap 13A) is applied to patient P, an actual (treatment) position of structure 13 relative to patient P may be measured or otherwise determined. In this sense, block 26 of method 20 may involve determining a treatment position of structure 13 in up to 6 degrees of freedom relative to the anatomy of patient P. The treatment position of structure 13 may be determined as described elsewhere herein. The treatment position of structure 13 may in turn specify the treatment locations 26A of transducers 12 based on the positional relationships between transducers 12 and structure 13. Once treatment locations 26A of transducers 12 are known, then treatment values 28A of transmission parameters for transducers 12 may be determined as described elsewhere herein (e.g. by interpolating intermediate values 24A previously determined for pre-treatment locations 31) or by analytical computation.

Figures 4A, 4B:
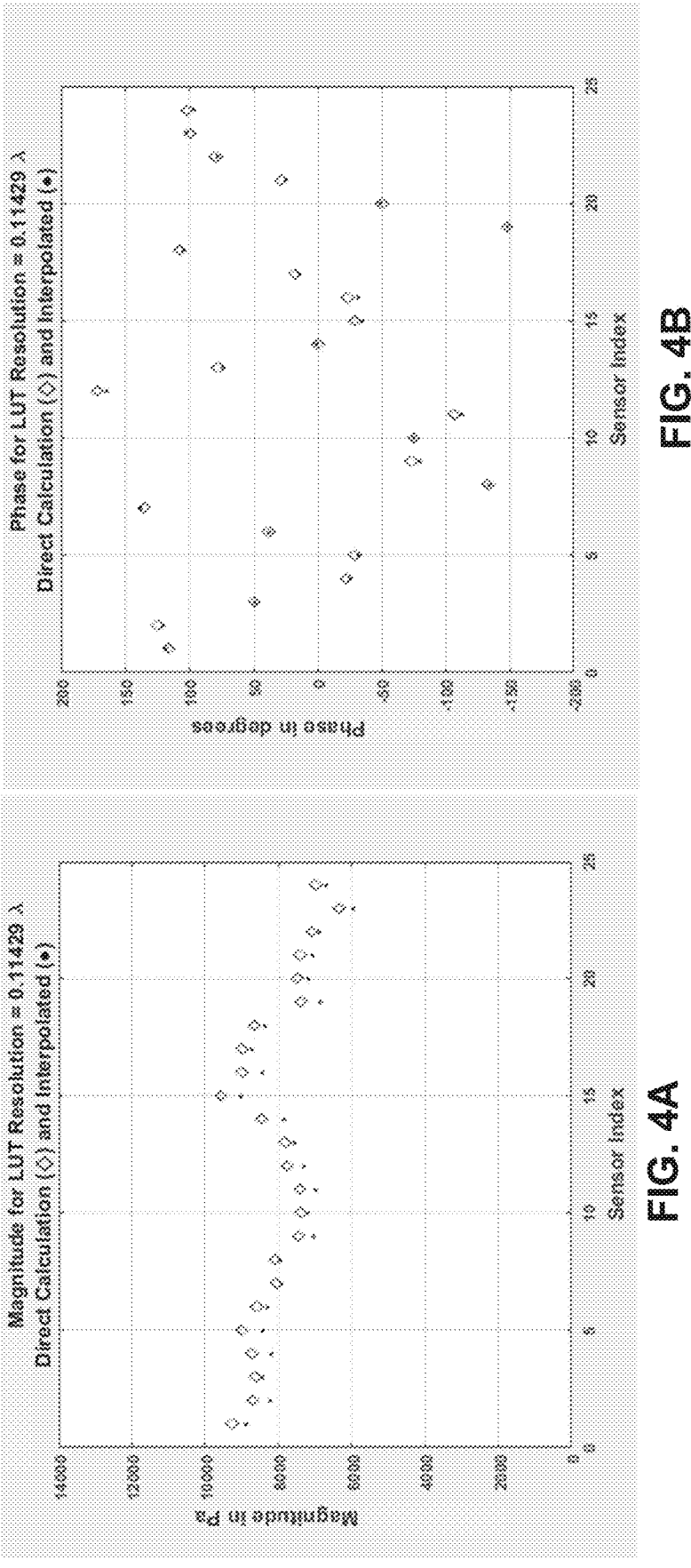
FIGS. 4A-4D are graphical illustrations of example ultrasound transmission parameters determined according to a particular embodiment of the method of FIG. 2 comprising interpolating intermediate values compared to ultrasound transmission parameters determined according to direct calculation techniques.

FIGS. 4A and 4B are example graphical representations respectively showing magnitude and phase pre-cursor treatment values determined using method 20 illustrated in FIGS. 2 and 3 where an interpolation technique is used to determine such pre-cursor treatment values in block 28. The values shown in FIGS. 4A and 4B are referred to herein as "pre-cursor treatment values, because the pre-cursor treatment values shown in FIGS. 4A and 4B are simulation parameters (from target T to treatment locations 26A) and may be converted (as described herein) to transmission parameters before being understood to be the block 28 treatment values 28A. In FIGS. 4A and 4B, amplitude and phase pre-cursor treatment values determined using method 20 are plotted using solid dots and are shown relation to amplitude and phase pre-cursor treatment values determined by direct calculation which are plotted using diamonds. In this context, "direct calculation" refers to the prior art technique of: applying structure 13 to patient P; determining the treatment locations of transducers 12; simulating propagation of ultrasound waves from a point source located at a target T to the treatment location of each transducer 12 using a suitable model of the patient's anatomy to thereby determine simulation parameters (pre-cursor treatment values) for each transducer 12; and converting the simulation parameters for each transducer 12 into corresponding transmission parameters. Direct calculation is similar to determining intermediate values 24A described elsewhere herein, except that treatment locations of transducers 12 after application of structure 13 to patient P are used in the place of pre-treatment locations 31.

FIGS. 4A and 4B show, for example, that if the three-dimensional (3D) voxel size for pre-treatment locations 31 (or discretization of pre-treatment locations for structure 13) is sampled at 0.11429*λ (where λ is the wavelength of the treatment ultrasound beam), then the magnitude and phase pre-cursor treatment values of transmission parameters for transducers 12 determined using method 20 illustrated in FIGS. 2 and 3 (based on interpolation in block 28) align well with directly calculated magnitude and phase pre-cursor treatment values—i.e. the magnitude is generally within 0.7 dB and phase is within 8.3°.

Figure 4D:
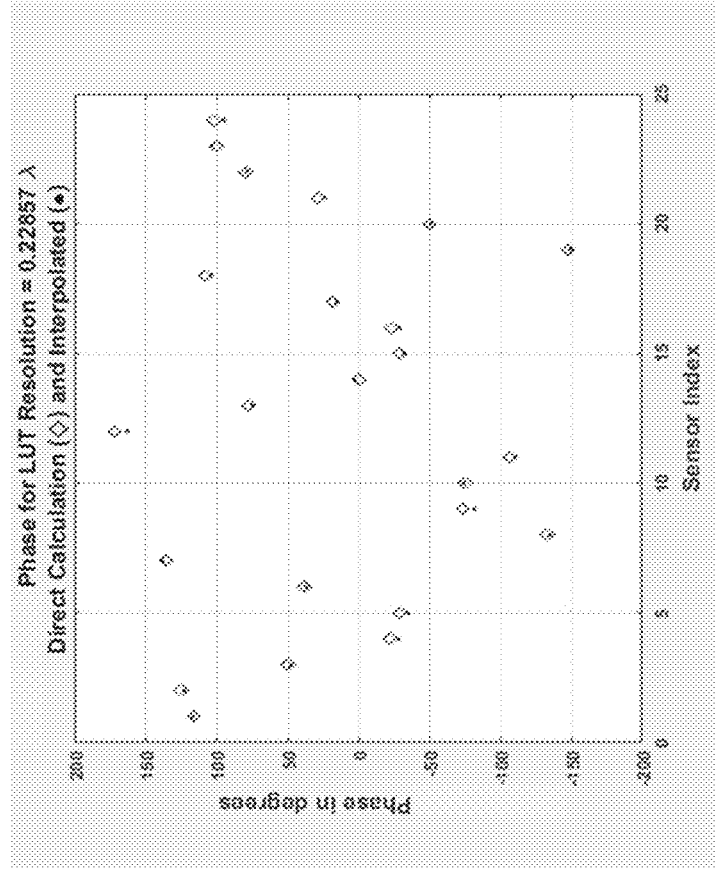
Figure 4C:
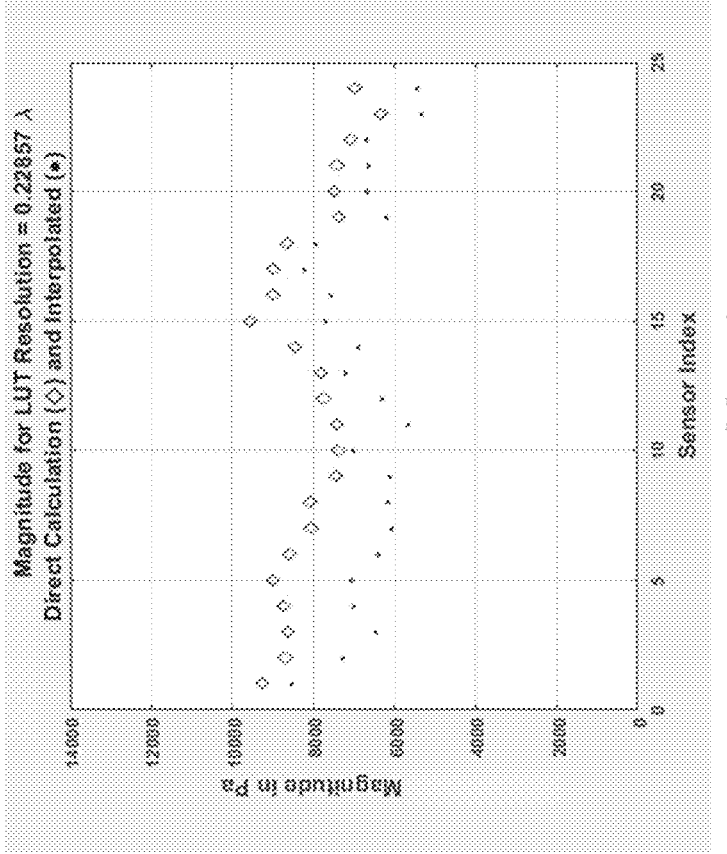

FIGS. 4C and 4D are example graphical representations like FIGS. 4A and 4B, except with coarser resolution (i.e. a voxel size for pre-treatment locations 31 (or discretization of pre-treatment positions for structure 13)) that is sampled at 0.22857*λ. With this coarser sampling size, the alignment between the magnitude and phase of the pre-cursor treatment values determined using method 20 illustrated in FIGS. 2 and 3 (based on interpolation in block 28) and directly calculated magnitude and phase pre-cursor treatment values is somewhat degraded (i.e. the magnitudes generally agree within 2.5 dB and phases within 8.9°).

In some embodiments, treatment values 28A may be determined in block 28 by suitable analytical computation (e.g. integration). Such analytical computation of treatment values 28A may be based on intermediate values 24A. Such analytical computation may also be based on pre-treatment locations 31 and treatment locations 26A of transducers 12. In some such embodiments, intermediate values 24A may be generated (e.g. in block 24) by calculating intermediate values 24A for pre-treatment locations 31 corresponding to a number of discretized surface patches on an intermediate surface.

Figure 5:
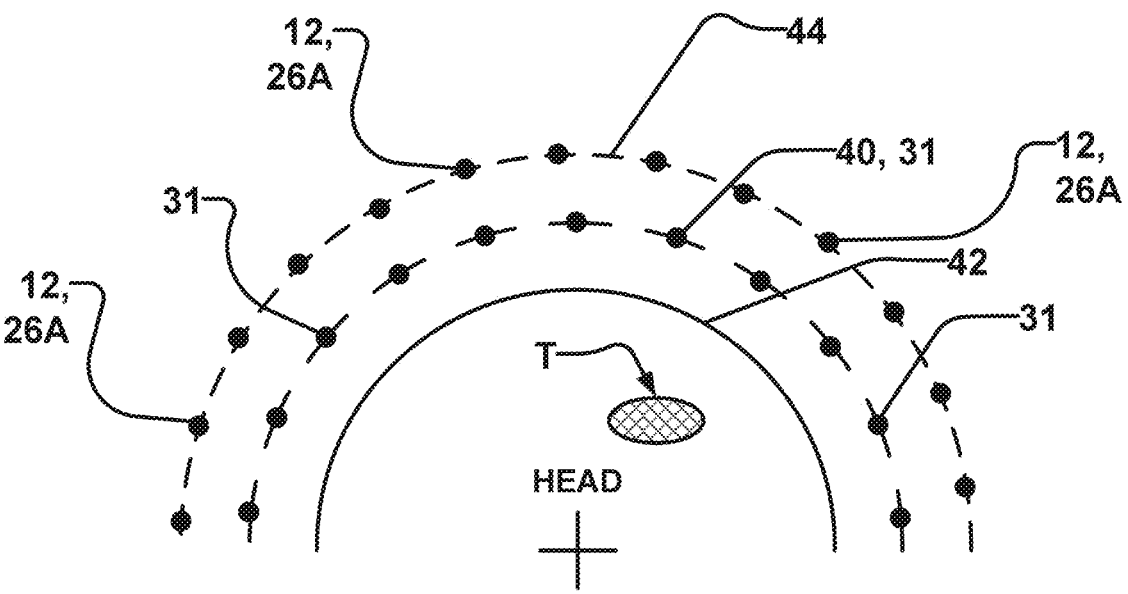
FIG. 5 is a schematic illustration of an example surface relative to a patient's head illustrating pre-treatment locations at which intermediate values may be determined according to an example embodiment of the invention.

FIG. 5 is a schematic illustration of a configuration where an analytical computation may be used for determining treatment values 28A in block 28. In the illustrated FIG. 5 embodiment, pre-treatment locations 31 are distributed on an intermediate surface 40, where intermediate surface 40 is shown schematically relative to skull surface 42. In the schematic illustration of FIG. 5, intermediate surface 40 is show as being semi-spherical, but this is not necessary in general, and intermediate surface 40 may generally have any shape. In some embodiments, the shape and/or position of intermediate surface 40 corresponds to the shape and/or position of skull surface 42.

Pre-treatment locations 31 may be defined for a number of discretized surface patches on intermediate surface 40. "Surface patch" means a portion of surface 40. That is, pre-treatment locations 31 may be discretized to correspond to the centers (or some other particular locations—e.g. particular corners) of discrete surface patches on surface 40. There may be a pre-treatment location 31 for each surface patch on surface 40. Surface 40 may generally be defined at any suitable location relative to the head of patient P. In some embodiments, surface 40 is closer to the head of patient P head than the expected treatment locations 26A of ultrasound transducers 12 or the treatment position of structure 13. In particular embodiments, surface 40 is positioned immediately adjacent (or substantially adjacent) the head of patient (or skull surface 42).

Calculating intermediate values 24A (in block 24) for each pre-treatment location 31 (e.g. surface patch) on surface 40 may be similar to that described above. Intermediate values 24A determined for each pre-treatment location 31 on surface 40 may comprise intermediate values 24A for simulation parameters (simulated from target T to pre-treatment locations 31) or intermediate values for transmission parameters (parameters that would cause an ultrasound beam originating from pre-treatment locations 31 to be focused at target T) as discussed above. It will be appreciated that the block 24 determination of intermediate values 24A may be performed in part 23 of method 20 before structure 13 is applied to the head of patient P (e.g. before cap 13A is put on the head of patient P).

After applying structure 13 to patient P (part 25 of method 20) and determining treatment locations 26A of transducers 12 (in a manner similar to that described elsewhere herein), an analytical computation may then be performed to determine treatment values 28A of transmission parameters in block 28. The block 28 analytical computation may be based on intermediate values 24A determined for surface 40, pre-treatment locations 31 on surface 40 and treatment locations 26A of transducers 12. Such an analytical computation of treatment values 28A may be fast (e.g. faster than direct calculation). Such an analytical computation may be fast (relative to direct calculation) because a distance between surface 40 and treatment locations 26A of transducers 12 can be small and because surface 40 may be chosen such that the intermediate media (e.g. acoustic coupling media) between treatment locations 26A of transducers 12 and surface 40 may comprise one or a few (e.g. 2 or 3) homogeneous layers, such as gel, water in a thin silicone bag with acoustic gel on the outside of the silicone bag and/or the like.

In some embodiments, the block 28 process of determining treatment values 28A of transmission parameters comprises applying a Kirchhoff Helmholtz integral (KHI) to the intermediate values 24A as follows:

$$\breve{p}(r) = j \int \int \breve{p}(r') \cos \phi \ (r, r') \left(1 - \frac{j}{k(r - r')}\right) \frac{e^{-jk(r-r')}}{\lambda(r - r')} dS' \tag{1}$$

where:
  S' is the pre-treatment surface (e.g. surface 40 in FIG. 5) that includes the surface patches and corresponding pre-treatment locations 31;
  r' are points on the surface S' (e.g. pre-treatment locations 31) with known complex pressures $\breve{p}(r')$ (e.g. known intermediate values 24A);
  $\breve{p}(r')$ are the complex ultrasound pressures (intermediate values 24A for an amplitude and phase) at locations r' which may be determined in block 24 by simulation (e.g. using an FDTD solver) based on patient model 22A;
  r are points not included in the surface S' corresponding to the treatment locations 26A of transducers 12;
  r-r' is the magnitude of the vector $\overrightarrow{r'r}$ pointing from the position r' to the position r;

cos $\phi$(r,r') is the cosine of the angle $\phi$(r,r') between a vector normal to the surface S' and the vector $\vec{r'r}$;

$\lambda$ is the wavelength of the treatment ultrasound energy;

$$k = \frac{2\pi}{\lambda}$$

is the wavenumber of the treatment ultrasound energy; and p̃(r) is complex ultrasound pressure at the treatment location 26A (r) due to acoustic energy at pre-treatment locations 31 (r') that are included in the integral. The complex ultrasound pressure p̃(r) may comprise values for simulation parameters which may be converted to treatment values 28A for amplitude and phase transmission parameters for an ultrasound beam emitted by a transducer 12 at treatment location 26A (r).

The equation (1) integral that may be performed in block 28 is over all points (e.g. over all pre-treatment locations 31 (r')) on the surface S' (e.g. surface 40 in the schematic illustration of FIG. 5). In some embodiments, the equation (1) integral may be performed in block 28 over a subset of the pre-treatment locations 31 (r') on the surface S', where the integral may be limited to pre-treatment locations 31 from which there is meaningful contribution to the treatment values 28A (p̃(r)) for a particular transducer 12 at a particular treatment location 26A (r). Pre-treatment locations 31 on surface S' may be excluded, for example, if there is no direct line of sight between the treatment location 26A (r) and a pre-treatment location 31 (r'). In addition, the directivity pattern of transducers 12 can also impact the number of pre-treatment locations 31 that need to be included in the equation (1) integral for a particular treatment location 26A (r). The directivity pattern determines how rapidly the sensitivity of a transducer 12 falls off as a function of angle; thus, if an acoustic source (e.g. an acoustic source placed at a pre-treatment location 31 (r')) is outside the angle dictated by the directivity pattern of a transducer 12 at a particular treatment location 26A (r), then that acoustic source may not contribute or contribute minimally to the treatment values 28A (p̃(r)).

Equation (1) as set out above applies where intermediate values 24A are intermediate values 24A for simulation parameters. Where intermediate values 24A are intermediate values 24A for simulation parameters, the output of such a KHI integral will yield integrated values of simulation parameters p̃(r) (pre-cursor treatment values as discussed herein) for treatment locations 26A of transducers 12. Such integrated values of simulation parameters (pre-cursor treatment values) can be converted (as part of block 28) into treatment values 28A of transmission parameters. This block 28 conversion of integrated values of simulation parameters (pre-cursor treatment values as discussed herein) into treatment values 28A of transmission parameters may be similar to the conversion of intermediate values 24A of simulation parameters into intermediate values 24A of transmission parameters discussed above in connection with block 24, except that treatment locations 26A may be used in the place of pre-treatment locations 31.

As discussed above, in some embodiments, the space between the head of patient P and the treatment locations 26A of ultrasound transducers 12 (e.g. between skull surface 42 and/or intermediate surface 40 and treatment locations 26A in the schematic illustration of FIG. 5) may be filled with a suitable ultrasound-transmitting medium (e.g. ultrasound-transmitting gel and/or water in silicone jacket and/or the like). Filling the space with such ultrasound-transmitting media may, for example, reduce complexities of applying an analytical computation, such as the KHI integral of equation (1). In some embodiments, system 10 or structure 13 comprises a fillable member (e.g. a fillable silicone jacket) which can be filled (e.g. with water or another ultrasound-transmitting liquid or gel) to fill the space between the head of patient P and the treatment locations 26A of ultrasound transducers 12 (e.g. between skull surface 42 and/or intermediate surface 40 and treatment locations 26A in the schematic illustration of FIG. 5). In some embodiments, the fillable member is as described in international PCT publication No. WO 2021/154730 entitled ULTRASOUND TRANSDUCER ASSEMBLY which is hereby incorporated by reference for all purposes.

Figure 6A:
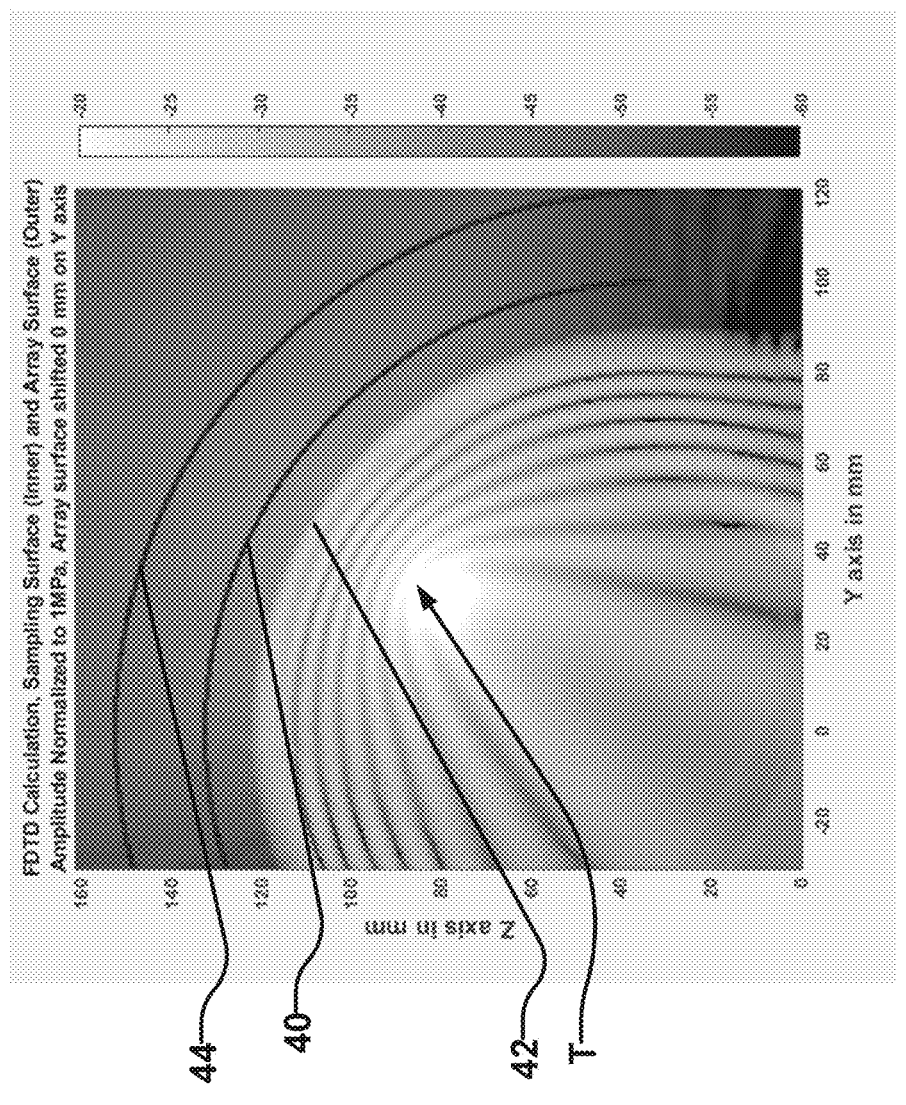
FIG. 6A is a graphical representation of an example ultrasound wave pattern.
Figures 6B, 6C:
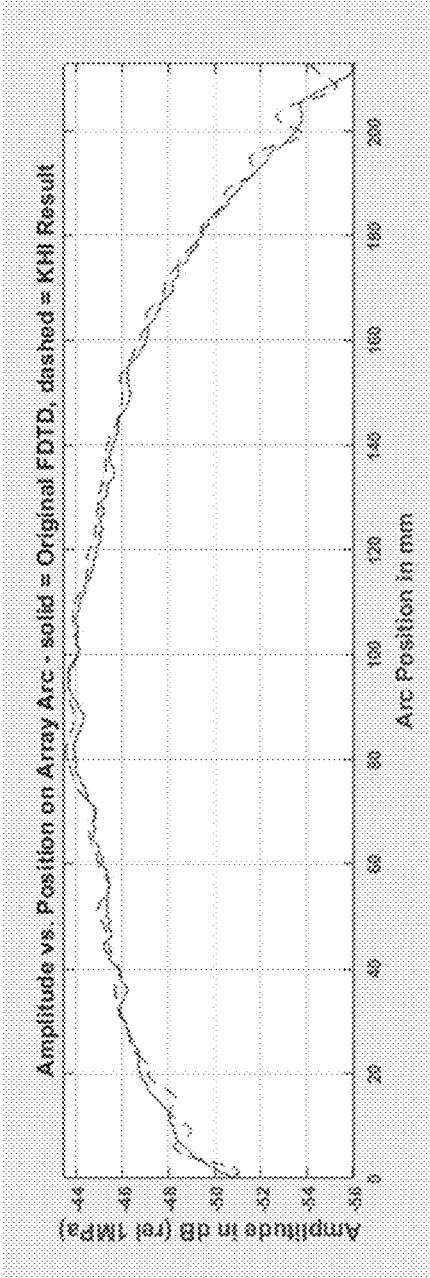
FIGS. 6B and 6C are graphical illustrations of example ultrasound transmission parameters determined according to a particular embodiment of the method of FIG. 2 comprising applying an analytical computation based on intermediate values compared to ultrasound transmission parameters determined according to direct calculation techniques.
Figure 6D:
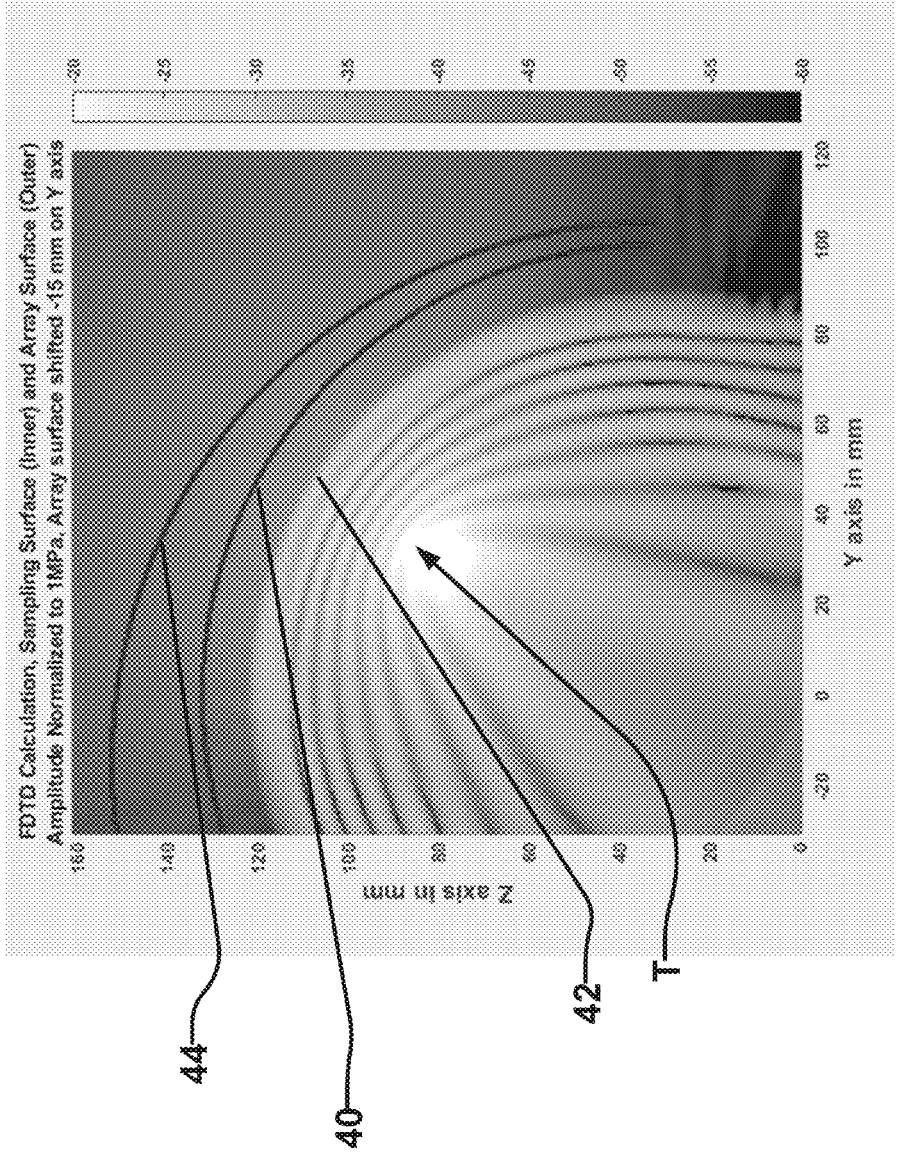
FIG. 6D is a graphical representation of an example ultrasound wave pattern.
Figure 6E:
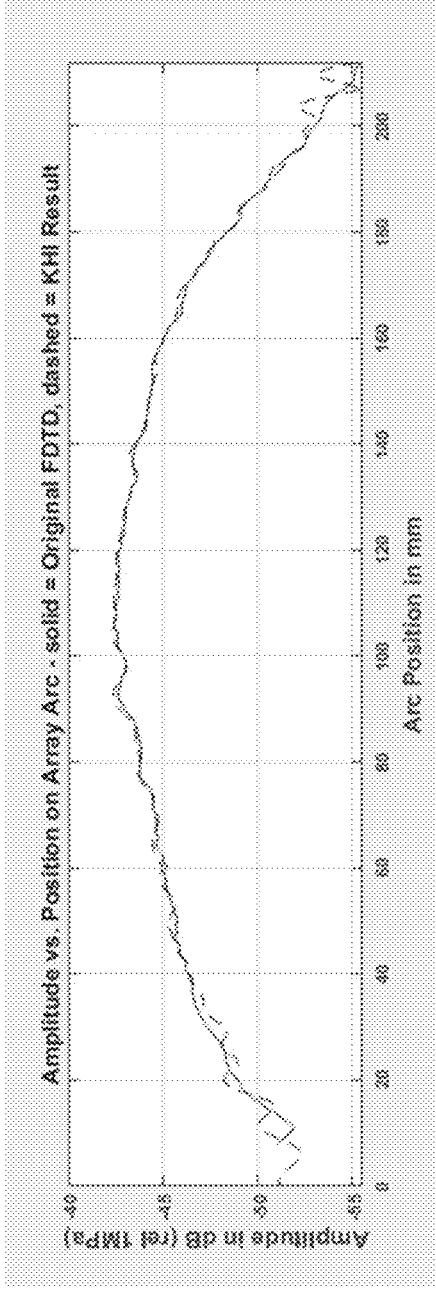
FIGS. 6E and 6F are graphical illustrations of example ultrasound transmission parameters determined according to a particular embodiment of the method of FIG. 2 comprising applying an analytical computation based on intermediate values compared to ultrasound transmission parameters determined according to direct calculation techniques.
Figure 6F:
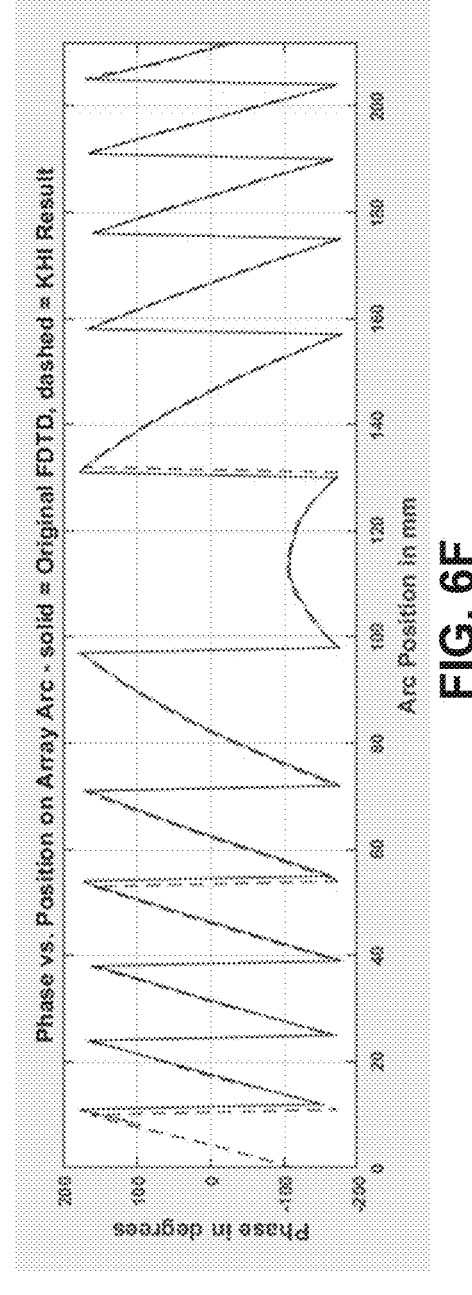

FIG. 6A is a graphical representation of an example ultrasound wave pattern showing surface 40, skull surface 42 and a surface 44 corresponding to treatment locations 26A of transducers 12—see the schematic illustration of these surfaces in FIG. 5. Although FIG. 6A shows transducers 12 having treatment locations 26A that have been illustrated as being on a smooth surface 44, treatment locations 26A need not be on a smooth surface in general. FIGS. 6B and 6C graphically illustrate example pre-cursor treatment values of transmission parameters (amplitude and phase transmission parameters) determined using the equation (1) KHI technique in block 28 (dashed lines) together with corresponding directly calculated pre-cursor treatment values (solid lines). The values shown in FIGS. 6B and 6C are referred to herein as "pre-cursor" treatment values, because the pre-cursor values shown in FIGS. 6B and 6C are simulation parameters and may be converted (as described herein) to transmission parameters before being understood to be the block 28 treatment values 28A. FIGS. 6B and 6C illustrate that the methods based on the KHI of equation (1) exhibit acceptable agreement with the more time-consuming direct calculation results. FIGS. 6D, 6E and 6F are similar to FIGS. 6A, 6B and 6C respectively, except that, in FIGS. 6D, 6E and 6F, the curve 44 corresponding to treatment locations 26A of transducers 12 is shifted by −15 mm on the Y-axis relative to the treatment locations 26A in FIGS. 6A, 6B and 6C (as shown best by comparing FIGS. 6A and 6D). Even for this case shown in FIGS. 6D, 6E and 6F, the agreement between the directly calculated pre-cursor treatment values and pre-cursor treatment values determined using the KHI integral of equation (1) exhibit acceptable agreement.

For comparison purposes, direct calculation of transmission parameters based on simulating reverse propagation of acoustic paths (e.g. a Finite-Difference Time-Domain ("FDTD") method), is complex and may consume a relatively large amount of time and/or computational resources because, for example, it requires calculating the acoustic field through the anatomical volume between a target T and treatment transducer locations. Prior art use of direct calculation techniques to determine transmission parameters for transducers requires that the transducers be located in their treatment locations (e.g. after structure 13 is applied to patient P) to facilitate the FDTD simulation. As mentioned above, there is a general desire to minimize, reduce and/or keep to an acceptable level, the time that it takes to determine treatment values of the transmission parameters after the application of structure 13 to patient P (e.g. after cap 13A is placed on the head of patient P).

The techniques described herein may involve the use of the FDTD method to determine intermediate values 24A for a number of pre-treatment locations 31, but determination of intermediate values 24A and such use of the FDTD technique is limited to part 23 of method 20 (i.e. before structure 13 is applied to patient P). Then, treatment values 28A for transmission parameters may be determined in block 28 in part 25 of method 20 (i.e. after structure 13 is applied to patient P) using, for example, the interpolation or KHI techniques described above. To illustrate the benefits of the interpolation method and the KHI method, example configurations are described below. In these example configurations, the sampling grid in the volume where the pre-treatment calculations are to be performed to determine intermediate values 24A (i.e. the discretization of pre-treatment locations 31) is spaced at about $\frac{1}{10}$ of an acoustic wavelength, or about 0.7 mm at 220 kHz. Also in this example, it is assumed that the radius of surface 33 (FIG. 3) and surface 44 (FIG. 5) is 200 mm. We also assume that these surfaces are hemispheres. We further assume that surface 32 (FIG. 3) and surface 40 (FIG. 5) are placed immediately adjacent to the head of patient P and that the radius of these surfaces is 120 mm and that these surfaces are also hemispherical.

With these assumptions, the encompassed volume between surfaces 32 and 33 (FIG. 3) would be $$\frac{1}{2} * \frac{4}{3}\pi * 200^3.$$

Now if this volume is sampled on 0.7 mm then the number of points (i.e. the number of pre-treatment locations 31) where FDTD is performed to determine intermediate values 24A is $$\frac{\frac{1}{2} * \frac{4}{3}\pi * 200^3}{0.7^3} = 48.8E^6.$$

For the interpolation technique described above, these ~48.8E⁶ pre-treatment calculations can be done in part 23 of method 20—i.e. prior to application of structure 13 to patient P. Now, when method 20 performs block 28, for each treatment location 26A, we only need to consider a relatively small number (as an example 8) neighboring pre-treatment locations 31 for the interpolation. So, by way of example, if structure 13 was to support 500 transducers 12 capable of transmitting therapeutic energy, then the total number of pre-treatment locations 31 to consider (after application of structure 13 to patient P in part 25 of method 20) would be 500×8=4,000 pre-treatment locations 31.

For the KHI technique described above, the FDTD technique to determine intermediate values 24A in block 24 need only be performed for points on surface 40 (FIG. 5). Thus, using the example geometries and sampling interval (0.7 mm) described above, a hemispherical surface of radius 120 mm would have ($\frac{1}{2}$*4*$\pi$*120²)/0.7²=185E³ pre-treatment locations 31. Once again, these pre-treatment calculations can be done in part 23 of method 20—i.e. prior to application of structure 13 to patient P. Then, after application of structure 13 to patient P, in block 28, for treatment transducer location 26A, we only need to perform the KHI over a subset of the pre-treatment locations 31, because, as discussed above, we may exclude pre-treatment locations 31 from which there may be no meaningful contribution. This can happen for example if there is no direct line of sight between the treatment transducer location 26A and a pre-treatment location 31 on surface 40. In addition, the directivity pattern of transducers 12 can also impact the number of pre-treatment locations 31 that need to be included. The directivity pattern determines how quickly the sensitivity of a transducer 12 falls off as a function of angle; thus, if a sound source (e.g. pre-treatment location 31) is outside the angle dictated by the directivity pattern of a transducer 12 located at a treatment location 26A, then that sound source may not contribute or contribute minimally to the acoustic pressure detected by the transducer 12.

Considering a directivity pattern of +/−15° subtended by the treatment locations 26A of transducers 12 (e.g. on surface 44), a calculation can now be performed as to how many surface 40 pre-treatment locations 31 should be included in the KHI integral. Given the example values of the radius of surface 44 to be 200 mm, and the radius of surface 40 to be 120 mm, the surface area of the base of a cone that intersects with surface 40 can be calculated. The vertex of the cone may be at the treatment transducer location 26A (e.g. on surface 44) and the angle of the cone may be +/−15°. The surface area of the base slightly underestimates the actual intersecting surface area of surface 40 with the cone, but it suffices as an example. With this understanding, the surface area of the base is calculated to be ~1438 mm². Since the entire surface area of surface 40 is 2*$\pi$*120² mm² and this had 185E³ pre-treatment locations 31, a surface area of 1438 mm² will have about 2940 pre-treatment locations 31. Thus, if structure 13 supports 500 treatment transducer 12, the total number of pre-treatment locations 31 to consider would be 500×2940~1470E³ pre-treatment locations 31. For the KHI, this number can be significantly reduced by placing structure 13 (e.g. surface 44) closer to surface 40.

Figure 7:
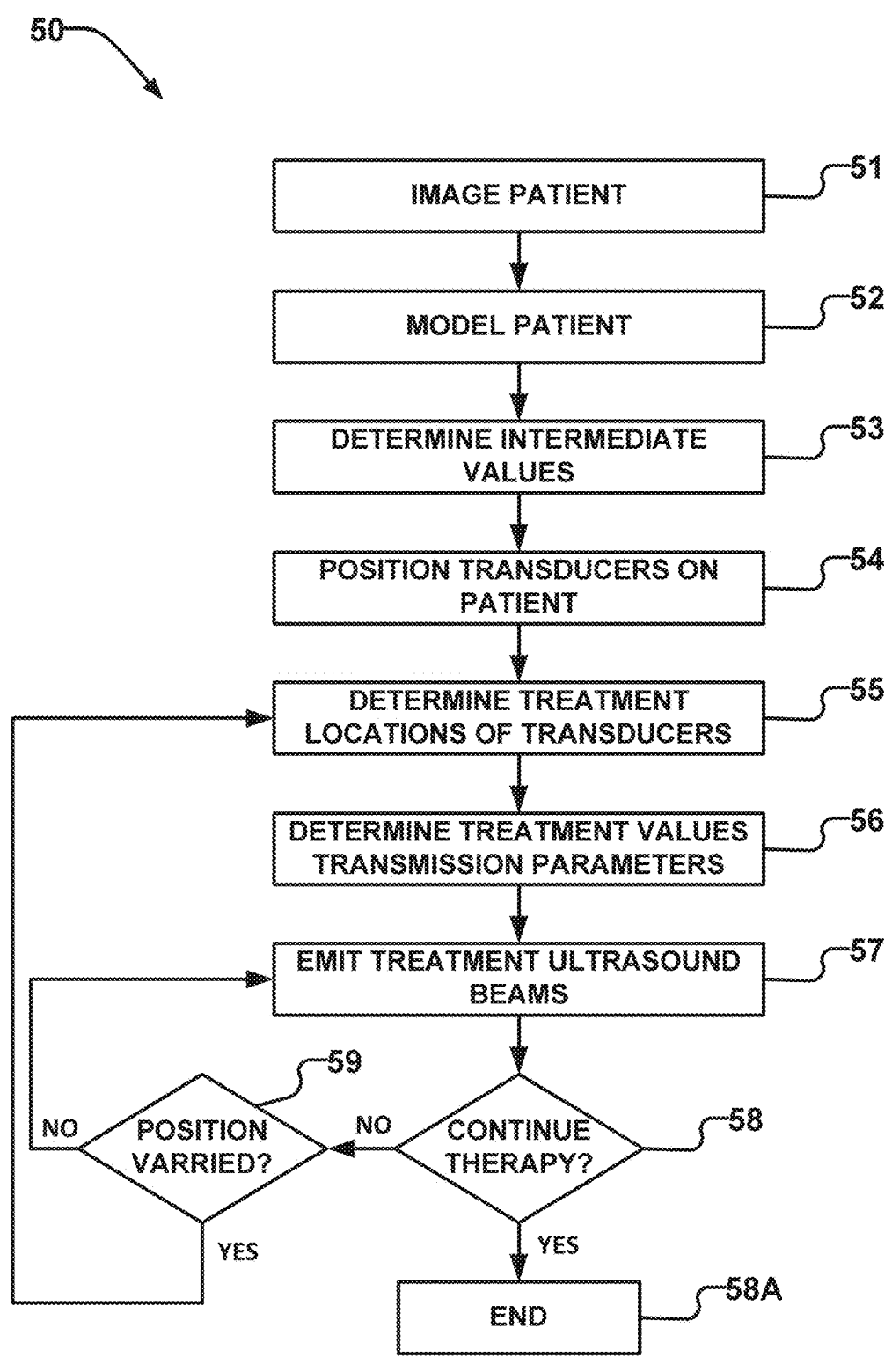
FIG. 7 is a block diagram illustrating a method according to an example embodiment of the invention.

FIG. 7 is a block diagram illustrating an example method 50 for applying ultrasound energy to a patient. In many respects, method 50 is similar (or has similar steps) to method 20 described above and where steps of method 50 are described as being similar to steps of method 20, then method 50 should be considered to incorporate any description of or variation of the corresponding steps of method 20.

In block 51 the patient is imaged. For example, one or more pre-treatment images of the head of the patient may be collected. As described elsewhere herein, the image data may comprise CT and/or MRI images of the patient's head or images taken with any other suitable technology. The patient may be imaged several hours or days prior to a scheduled ultrasound treatment or several weeks or months prior. In some embodiments, image data is provided as input to method 50, in which case imaging in block 51 is not required.

A model of the patient's head is generated from the image data in block 52. The model may be analogous to patient model 22A described herein and may be generated as described elsewhere herein (e.g. as described in connection with block 22 of method 20 (FIG. 2)). In some embodiments, the model of the patient's head is provided as input to method 50, in which case model generating block 52 is not required.

Block 53 comprises determining intermediate values which may be analogous to intermediate values 24A described herein and may be determined as described elsewhere herein (e.g. as described in connection with block 24 of method 20 (FIG. 2)). As discussed above in connection with block 24 and intermediate values 24A, the block 53 intermediate values may be based on pre-treatment locations 31 and the block 52 model. As discussed above in connection with block 24 of method 20, the block 53 intermediate values may comprise intermediate values for simulation parameters (simulated from target T to pre-treatment locations 31) or intermediate values for transmission parameters (parameters that would cause an ultrasound beam originating from pre-treatment locations 31 to be focused at target T).

In block 54 ultrasound transducers (e.g. transducers 12) are positioned around the patient's head. This block 54 procedure may comprise applying structure 13 to the head of patient P (e.g. putting cap 13A on the head of patient P).

Block 55 comprises measuring or otherwise determining treatment locations of the ultrasound transducers 12. The block 55 treatment transducer locations may be analogous to treatment locations 26A described herein and may generally be determined using any suitable technique, including, without limitation, any of those described in connection with block 26 of method 20 (FIG. 2) or elsewhere herein. Block 55 may comprise determining a treatment position of structure 13 (e.g. cap 13A) in any of up to 6 degrees of freedom. Where the locations of transducers 12 are known relative to the position of structure 13, the treatment locations of transducers 12 may be determined from the treatment position of structure 13. In general, the block 55 treatment transducer locations may be determined by any suitable technique.

Block 56 involves determining treatment values of transmission parameters for ultrasound transducers 12. The block 56 treatment values of transmission parameters may be analogous to treatment values 28A described herein and may generally be determined using any of the techniques described in connection with block 28 of method 20 (FIG. 2) or elsewhere herein. The block 56 treatment values may be determined based in part on the block 53 intermediate values (determined for pre-treatment locations). The block 56 treatment values may be determined based in part on the pre-treatment locations (for which the block 53 intermediate values are determined). The block 56 treatment values may be determined based in part on block 55 treatment locations of the ultrasound transducers 12. As described in more detail below, the block 56 treatment values may be determined or updated in real time.

In block 57, treatment ultrasound beams having the block 56 treatment values for transmission parameters of ultrasound transducers 12 are applied to the patient's head (e.g. to open the blood-brain barrier at a desired location).

Block 58 evaluates whether further ultrasound beams are to be applied or whether treatment should be ended. Treatment may be ended, for example, if a threshold amount of time has elapsed, a desired amount of ultrasound energy has been delivered to a desired target, the blood-brain barrier has been successfully opened, etc. If treatment is to be ended (block 58 YES branch), method 50 proceeds to block 58A, where treatment is ended. Otherwise, method 50 proceeds (via the block 58 NO branch) to block 59.

Block 59 evaluates (e.g. in real time, although this is not necessary) whether a treatment location of at least one of the ultrasound transducers 12 (or the treatment location of structure 13) has varied or varied by more than a configurable threshold amount (e.g. by more than $\frac{1}{16}^{th}$, $\frac{1}{8}^{th}$, $\frac{1}{4}^{th}$, etc. of the wavelength of the treatment ultrasound beam). In some embodiments, to perform the block 59 evaluation, block 59 may involve determining updated treatment locations of transducers 12 and/or treatment location structure 13 in a manner analogous to that of block 55 (or analogous to block 26 of method 20) and comparing such updated treatment location(s) to previous treatment location(s) determined, for example, in a last iteration of block 55. In some embodiments, the block 59 inquiry may be performed using other techniques and/or sensors. By way of non-limiting example, ultrasound system 10 may comprise one or more proximity sensors (e.g. one on the head of patient P and one on structure 13) which may determine if the position of structure 13 has moved relative to the head of patient P in block 59. By way of non-limiting example, such proximity sensors may comprise retro-reflective ultrasonic sensors and/or the like. The electronics for such sensor could be supported by structure 13. The same or different sensors (proximity sensors or other sensors) may be used to determine how much relative movement has occurred between structure 13 and the head of patient P. Relative movement between structure 13 and the head of patient P that is greater than a threshold may lead to the block 59 YES branch.

If the block 59 inquiry is negative and the treatment locations of transducers 12 have not varied by more than a threshold amount, then method 50 returns to block 57 and emission of ultrasound continues (e.g. to the same target T in the brain of the patient). If, on the other hand, the block 59 inquiry is positive and the treatment location of a transducer 12 has moved by more than a threshold amount, then method 50 may return to block 55, where the procedures of blocks 55, 56 and 57 may be repeated. In some embodiments, the updated treatment transducer locations determined as part of block 59 may be adopted in block 55—that is, it may not be necessary to repeat all of the procedures of block 55 described above if the treatment transducer locations have just been determined in block 59.

In some embodiments, after the block 59 inquiry determines that a treatment location of a transducer 12 has moved (block 59 YES branch), the procedures of blocks 55 and 56 are repeated and ultrasound is emitted with new treatment values in block 57 (e.g. to the same target location T) without disruption of ultrasound treatment—e.g. ultrasound treatment is continuously applied while updates to treatment values are incorporated (e.g. in real time). In some embodiments, blocks 55 and 56 may be performed during the "off" portion of the duty cycle of the block 57 ultrasound emission (e.g. between ultrasound pulses). In some embodiments, the block 57 ultrasound emission may occur with previously determined treatment values (e.g. treatment values determined in a previous iteration of block 56) until new treatment values are determined in block 56 for the new treatment locations of transducers 12. In this manner, real time feedback related to the treatment locations of transducers 12 is incorporated into the treatment values of the method 50 ultrasound treatment. This real time feedback may be facilitated by the rapid determination of treatment values (in block 56) which, in turn, may be facilitated by the pre-treatment determination of intermediate values (in block 53) based on pre-treatment locations and the block 52 model. In some embodiments, block 57, 58 and 59 (and if necessary pursuant to the block 59 inquiry, blocks 55 and 56) may be being continuously performed (e.g. in real time and/or in the background) while ultrasound treatment focused at the target location T is being continuously applied to patient P in block 57.

In the context of this specification, the concept of "real time" may be understood to be within one "treatment period". Typically, ultrasound treatment is delivered with a duty cycle, where there is an acoustic pulse or acoustic signal that is delivered for a first time ($t_{on}$) and then there is a rest period ($t_{off}$) during which no acoustic energy is delivered and then this pattern of acoustic pulses (of duration $t_{on}$) and rests (of duration $t_{off}$) may be repeated for some suitable length of time (a treatment time). The sum of the durations $t_{on}$ and $t_{off}$ ($t_p=t_{on}+t_{off}$) may be referred to herein as the "treatment period" ($t_p$). The ratio of $t_{on}/t_p$ is the duty cycle. In the context of this specification, the concept of "real time" may be understood to be within one "treatment period". In some embodiments, blocks 58 and 59 (and if necessary pursuant to the block 59 inquiry, blocks 55 and 56) may be performed to update the treatment values for the transmission parameters of ultrasound transducers 12 in real time. Such real time updates to the treatment values for the transmission parameters of ultrasound transducers 12 may occur while ultrasound treatment is being applied to patient P in block 57.

In some embodiments, if the block 59 inquiry determines that a treatment location of a transducer 12 has moved (block 59 YES output) or if the block 59 inquiry determines that a treatment location of a transducer 12 has moved by an amount that is sufficiently large (e.g. by a suspension threshold amount, where the suspension threshold amount is greater than the above-discussed threshold amounts for block 59), then the application of ultrasound therapy may be suspended or discontinued—e.g. until new treatment values are determined in another iteration of block 56 (possibly after new treatment locations are determined in block 55 or in block 59), whereupon the application of ultrasound therapy (treatment ultrasound energy) may be restarted.

Method 50 is presented in a particular logical order for ease of explanation. In some implementations, various functional blocks of method 50 may be performed in a different order or in a different logical flow. For example, the block 59 evaluation may be performed continually (e.g. in the background) while treatment ultrasound energy is delivered in block 57. If the block 59 evaluation determines that relative movement between patient P and transducers 12 has occurred, then it may interrupt the delivery of treatment ultrasound in block 57 or may return to block 55 as described above.

As discussed above, ultrasound system 10 may comprise proximity sensors for evaluating relative movement between transducers 12 (or structure 13) and patient P. Such proximity sensors may be arranged or otherwise configured to obtain a measure of how much relative motion has occurred between transducers 12 (or structure 13) and patient P. As an example, the beam of a retro-reflective ultrasonic proximity sensor can be arranged so that the beam width is ⅛, ¼, ½, or 1 times the wavelength of the therapy ultrasound beam. If the therapy ultrasound beam is at 220 KHz, then the wavelength is approximately 7 mm. Thus, the beam of the ultrasonic proximity sensor may be arranged (by using the appropriate frequency, transducer size, lens focusing) to some fraction of 7 mm. For example, the beam of the ultrasonic proximity sensor may be arranged to be 7 mm. Now, the ultrasound reflector can be for example 1 mm. This means that if the reflector is anywhere within the 7 mm beam of the ultrasound proximity sensor, a reflection from the reflector may be obtained. However, if the reflector is outside this 7 mm beam, there may be diminished or no reflection. This arrangement can be used to estimate (e.g. in block 59) if the relative motion of transducers 12 (or structure 13) relative to the patient P after the initial block 55 has been executed is more than +/−3.5 mm (assuming that the reflector was placed at the center of the beam from the ultrasound proximity sensor). Thus, method 50 can be configured to continue emitting treatment radiation in block 57 if the relative motion is less than +/−3.5 mm (a block 59 negative evaluation) and method 50 can be caused to return to block 55 or halted if the relative motion is more than +/−3.5 mm (a block 59 positive evaluation).

With other configurations of proximity sensors, it may be possible to measure the magnitude and orientation of the relative motion between transducers 12 (or structure 13) and patient P. In particular, this may be achievable for small distances relative to the wavelength of the ultrasound therapy beam. Where the proximity sensors provide the magnitude and orientation of relative movement between transducers 12 (or structure 13) and patient P, updated treatment locations of transducers 12 may be determined in block 55 based on this information from the proximity sensors. These updated treatment locations of transducers 12 may then be used in block 56 to determine updated treatment values for transducers 12. Updated treatment values determined in block 56 may then be used for subsequent emission of treatment ultrasound in block 57. Such procedures can be performed without interrupting the block 57 treatment. In some embodiments, blocks 55 and 56 may be performed during the "off" portion of the duty cycle of the block 57 ultrasound emission. In some embodiments, the block 57 ultrasound emission may occur with previously determined treatment values until new treatment values are determined in block 56.

In some embodiments involving the block 57 application of treatment ultrasound energy to patient P and where there are a plurality of target locations $T_1, T_2, \ldots T_M$, ultrasound energy is delivered (e.g. in block 30) for a first target T, while the steps of block 56 (and optionally block 55) may be used to determine treatment values for transmission parameters of transducers 12 for a subsequent target. That is, treatment values for one or more subsequent targets are being determined (e.g. according to the procedures of block 56 described herein) while treatment ultrasound is being delivered to a first target. In some embodiments, the sets of transducers 12 used for each target $T_1, T_2, \ldots T_M$ may be, but need not be, the same. If the transducers 12 used for different targets $T_1, T_2, \ldots T_M$ are not the same, then block 55 may be used to determine treatment locations of the set of transducers 12 involved for each target $T_1, T_2, \ldots T_M$ while treatment ultrasound energy is being delivered in block 57. In some embodiments, a first iteration of block 55 may determine positions for all of the transducers 12 which may be used for different targets $T_1, T_2, \ldots T_M$, in which case block 55 need not be performed separately for the set of transducers 12 involved for each target $T_1, T_2, \ldots T_M$.

It will be appreciated from the above discussion of method 50 of FIG. 7 that the feedback portions of method 50 (e.g. block 58 and/or block 59) could be incorporated into method 20 of FIG. 2 to facilitate real-time feedback related to treatment locations of transducers into method 20 while permitting continuous delivery of treatment ultrasound to patient P.

The description set out above describes a method for determining treatment values for the transmission parameters for transmit ultrasound transducers which reduces the time and computational resources that it takes to make such determination after the application of structure 13 to patient P, which is a desirable outcome for reasons discussed above. In some applications, it can be desirable to ascertain expected parameters (e.g. phase and/or other parameters) of reflected ultrasound energy received at receive transducers 18 (see FIG. 1). Methods analogous to those described herein for treatment values for the transmission parameters for transmit ultrasound transducers may be used for determining expected receive parameters at receive transducers 18. For example, intermediate values of expected receive parameters may be computed (before application of structure 13 to patient P) for pre-treatment locations of receive transducers 18 and then, after application of structure 13 to patient P, such intermediate values can be processed based on actual locations of receive transducers 18 (e.g. by interpolation, integration or otherwise) to obtain the actual values of expected receive parameters at the actual locations of receive transducers 18. As is the case for treatment values for the transmission parameters for transmit ultrasound transducers, such techniques can reduce the time associated with determining the actual values of expected receive parameters at receive transducers 18 after structure 13 is applied to patient 13.

Figure 8:
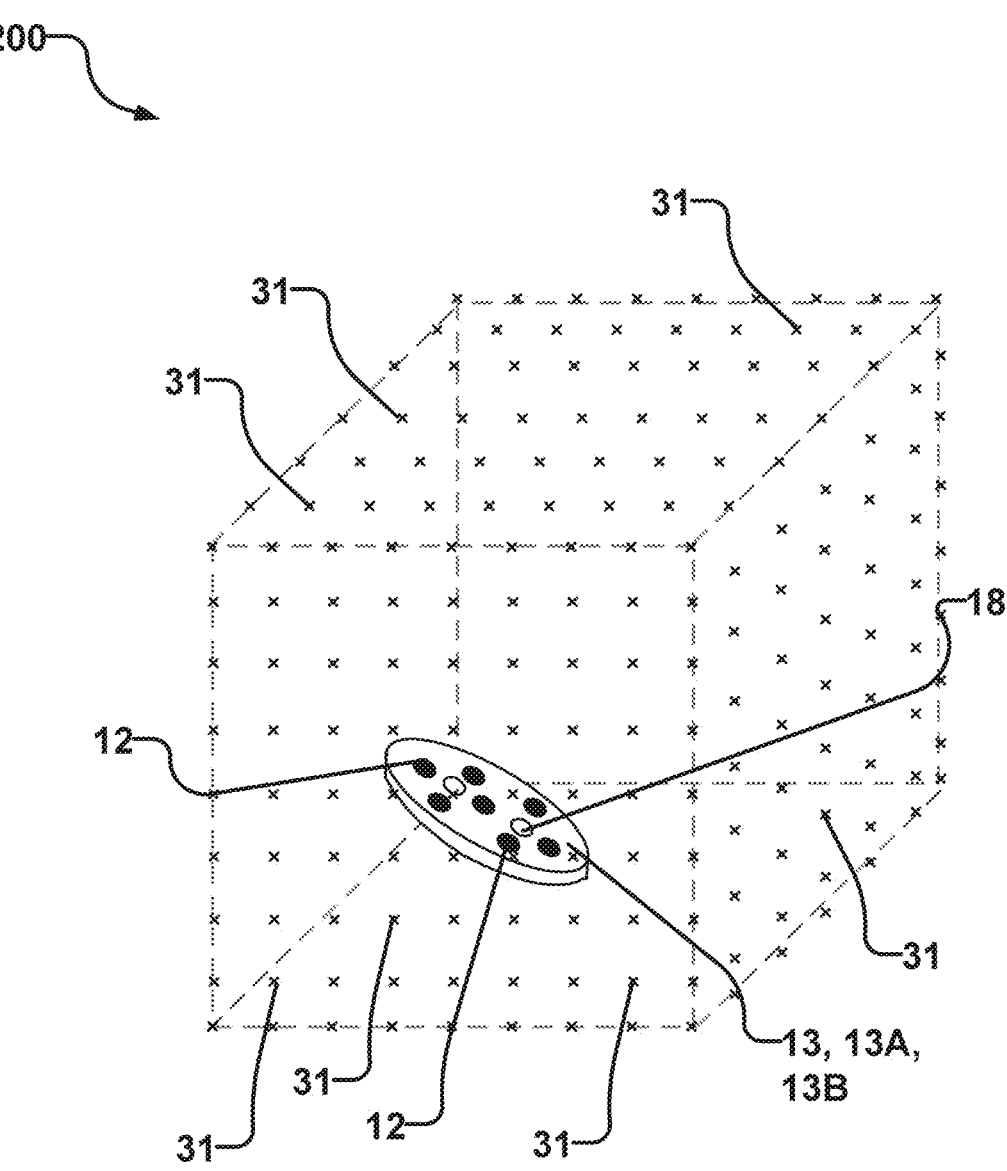
FIG. 8 is a schematic illustration of an ultrasound system according to an example embodiment of the invention.

FIG. 8 is a schematic illustration of an ultrasound system 200 to which the techniques described herein (e.g. method 20 of FIG. 2 and/or method 50 of FIG. 7) could be applied. Ultrasound system 200 is similar to ultrasound system 10 described elsewhere herein and, for brevity, this disclosure focuses on the differences between ultrasound system 200 and ultrasound system 10, it being understood that other features of ultrasound system 200 may be similar to those described for system Components of system 200 that are similar to those of system 10 described elsewhere herein are referenced using similar reference numerals. Ultrasound system 200 differs from ultrasound system 10 primarily in that ultrasound system 200 is shown to comprise a module 13B (which may be part of structure 13 and/or cap 13A) comprising one or more transmit transducers 12 and, optionally, one or more receive transducers 18. Structure 13 (or cap 13A) may comprise a plurality of modules 13B, each of which may comprise one or more transmit transducers 12 and/or one or more receive transducers 18. In general, ultrasound system 200 may emit focused treatment ultrasound energy using some or all transmit transducers 12 within module 13B. Ultrasound system 200 may emit focused treatment ultrasound energy using transmit transducers 12 that span multiple modules 13B.

Treatment values for transmission parameters for transducers 12 of ultrasound system 200 may be determined using methods similar to those of method 20 (FIG. 2) and/or method 50 (FIG. 7), where references to structure 13 and/or cap 13A may be understood to be applicable to module 13B. For brevity, method 20 is described here, it being understood that method 50 could be performed in an analogous manner. With respect to method 20 of FIG. 2, blocks 22 and 24 may be substantially similar to those described for ultrasound system 10. Block 24 may involve determining intermediate values 24A for a plurality of pre-treatment locations 31 (see FIG. 8). In some embodiments, the pre-treatment locations 31 may based on a number of pre-treatment positions of module 13B which may be specified relative to the anatomy of patient P in up to 6 degrees of freedom. Based on these pre-treatment positions of module 13B, pre-treatment locations 31 of transducers 12 may be specified based on the positional relationships of transducers 12 relative to module 13B and/or relative to one another. In some embodiments, pre-treatment locations 31 may based on a number of pre-treatment positions of structure 13 which may be specified relative to the anatomy of patient P in up to 6 degrees of freedom. Based on these pre-treatment positions of structure 13, the pre-treatment positions of module 13B and in turn the pre-treatment locations 31 of transducers 12 may be specified based on the positional relationships of module 13B relative to structure 13, and the positional relationships of transducers 12 relative to module 13B and/or relative to one another.

Structure 13 is then applied to patient P (block 25 method 20) and the treatment locations 26A of transducers 12 are determined in block 26. The treatment locations 26A of transducers 12 may be determined by any suitable technique. In some embodiments, the treatment locations 26A of transducers 12 may be determined based on measuring or otherwise determining a treatment position of module 13B relative to the anatomy of patient P in up to 6 degrees of freedom (e.g. where positional relationships between transducers 12 and module 13B are known). In some embodiments, the treatment locations 26A of transducers 12 may be determined based on measuring or otherwise determining a treatment position of structure 13 relative to the anatomy of patient P in up to 6 degrees of freedom (e.g. where positional relationships between module 13B and structure 13 and between transducers 12 and module 13B are known). Treatment locations 26A of transducers 12 can be determined by any suitable additional or alternative technique.

Treatment values 28A for the transmission parameters of transducers 12 may be determined in block 28 using any of the techniques described herein. Such techniques may be based in part on intermediate values 24A (determined for pre-treatment locations 31). In some embodiments, treatment values 28A for the transmission parameters of transducers 12 may be determined in block 28 by processing intermediate values 24A. Treatment values 28A may be determined in block 28 based in part on pre-treatment locations 31 (at which intermediate values 24A are determined). Treatment values 28A may be determined based in part on treatment locations 26A of the ultrasound transducers 12.

It will be appreciated that the above-discussed features of ultrasound system 200 may be extended to method 50 (FIG. 7) in a manner analogous to that of ultrasound system 10 and that the above-discussed features of transmit transducers 12 of ultrasound system 200 may be extended to receive transducers 18 in a manner analogous to that of ultrasound system 10.

Where a component (e.g. a software module, process or, assembly, device, circuit, etc.) is referred to herein, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Embodiments of the invention may be implemented using specifically designed hardware, configurable hardware, programmable data processors configured by the provision of software (which may optionally comprise "firmware") capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs"), and the like. Examples of configurable hardware are: one or more programmable logic devices such as programmable array logic ("PALs"), programmable logic arrays ("PLAs"), and field programmable gate arrays ("FPGAs"). Examples of programmable data processors are: microprocessors, digital signal processors ("DSPs"), embedded processors, graphics processors, math co-processors, general purpose computers, server computers, cloud computers, mainframe computers, computer workstations, and the like. For example, one or more data processors in a control circuit for a device may implement methods as described herein by executing software instructions in a program memory accessible to the processors.

Processing may be centralized or distributed. Where processing is distributed, information including software and/or data may be kept centrally or distributed. Such information may be exchanged between different functional units by way of a communications network, such as a Local Area Network (LAN), Wide Area Network (WAN), or the Internet, wired or wireless data links, electromagnetic signals, or other data communication channel.

The invention may also at least partially be provided in the form of a program product. The program product may comprise any non-transitory medium which carries a set of computer-readable instructions which, when executed by a data processor, cause the data processor to execute a method of the invention. Program products according to the invention may be in any of a wide variety of forms. The program product may comprise, for example, non-transitory media such as magnetic data storage media including floppy diskettes, hard disk drives, optical data storage media including CD ROMs, DVDs, electronic data storage media including ROMs, flash RAM, EPROMs, hardwired or preprogrammed chips (e.g., EEPROM semiconductor chips), nanotechnology memory, or the like. The computer-readable signals on the program product may optionally be compressed or encrypted.

In some embodiments, the invention may be implemented in software. For greater clarity, "software" includes any instructions executed on a processor, and may include (but is not limited to) firmware, resident software, microcode, code for configuring a configurable logic circuit, applications, apps, and the like. Both processing hardware and software may be centralized or distributed (or a combination thereof), in whole or in part, as known to those skilled in the art. For example, software and other modules may be accessible via local memory, via a network, via a browser or other application in a distributed computing context, or via other means suitable for the purposes described above.

Software and other modules may reside on servers, workstations, personal computers, tablet computers, and other devices suitable for the purposes described herein.

Interpretation of Terms

Unless the context clearly requires otherwise, throughout the description and the claims:

"comprise", "comprising", and the like are to be construed in an inclusive sense, as opposed to an exclusive or exhaustive sense; that is to say, in the sense of "including, but not limited to";

"connected", "coupled", or any variant thereof, means any connection or coupling, either direct or indirect, between two or more elements; the coupling or connection between the elements can be physical, logical, or a combination thereof;

"herein", "above", "below", and words of similar import, when used to describe this specification, shall refer to this specification as a whole, and not to any particular portions of this specification;

"or", in reference to a list of two or more items, covers all of the following interpretations of the word: any of the items in the list, all of the items in the list, and any combination of the items in the list;

the singular forms "a", "an", and "the" also include the meaning of any appropriate plural forms. These terms ("a", "an", and "the") mean one or more unless stated otherwise;

"and/or" is used to indicate one or both stated cases may occur, for example A and/or B includes both (A and B) and (A or B);

"approximately" when applied to a numerical value means the numerical value ±10%;

where a feature is described as being "optional" or "optionally" present or described as being present "in some embodiments" it is intended that the present disclosure encompasses embodiments where that feature is present and other embodiments where that feature is not necessarily present and other embodiments where that feature is excluded. Further, where any combination of features is described in this application this statement is intended to serve as antecedent basis for the use of exclusive terminology such as "solely," "only" and the like in relation to the combination of features as well as the use of "negative" limitation(s)" to exclude the presence of other features; and "first" and "second" are used for descriptive purposes and cannot be understood as indicating or implying relative importance or indicating the number of indicated technical features.

Words that indicate directions such as "vertical", "transverse", "horizontal", "upward", "downward", "forward", "backward", "inward", "outward", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

Where a range for a value is stated, the stated range includes all sub-ranges of the range. It is intended that the statement of a range supports the value being at an endpoint of the range as well as at any intervening value to the tenth of the unit of the lower limit of the range, as well as any subrange or sets of sub ranges of the range unless the context clearly dictates otherwise or any portion(s) of the stated range is specifically excluded. Where the stated range includes one or both endpoints of the range, ranges excluding either or both of those included endpoints are also included in the invention.

Certain numerical values described herein are preceded by "about". In this context, "about" provides literal support for the exact numerical value that it precedes, the exact numerical value ±5%, as well as all other numerical values that are near to or approximately equal to that numerical value. Unless otherwise indicated a particular numerical value is included in "about" a specifically recited numerical value where the particular numerical value provides the substantial equivalent of the specifically recited numerical value in the context in which the specifically recited numerical value is presented. For example, a statement that something has the numerical value of "about 10" is to be interpreted as: the set of statements:

in some embodiments the numerical value is 10;

in some embodiments the numerical value is in the range of 9.5 to 10.5;

and if from the context the person of ordinary skill in the art would understand that values within a certain range are substantially equivalent to 10 because the values with the range would be understood to provide substantially the same result as the value 10 then "about 10" also includes:

in some embodiments the numerical value is in the range of C to D where C and D are respectively lower and upper endpoints of the range that encompasses all of those values that provide a substantial equivalent to the value 10.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

As will be apparent to those of skill in the art upon reading this disclosure, each of the individual embodiments described and illustrated herein has discrete components and features which may be readily separated from or combined with the features of any other described embodiment(s) without departing from the scope of the present invention.

Any aspects described above in reference to apparatus may also apply to methods and vice versa.

Any recited method can be carried out in the order of events recited or in any other order which is logically possible. For example, while processes or blocks are presented in a given order, alternative examples may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, simultaneously or at different times.

Various features are described herein as being present in "some embodiments". Such features are not mandatory and may not be present in all embodiments. Embodiments of the invention may include zero, any one or any combination of two or more of such features. All possible combinations of such features are contemplated by this disclosure even where such features are shown in different drawings and/or described in different sections or paragraphs. This is limited only to the extent that certain ones of such features are incompatible with other ones of such features in the sense that it would be impossible for a person of ordinary skill in the art to construct a practical embodiment that combines such incompatible features. Consequently, the description that "some embodiments" possess feature A and "some embodiments" possess feature B should be interpreted as an express indication that the inventors also contemplate embodiments which combine features A and B (unless the description states otherwise or features A and B are fundamentally incompatible). This is the case even if features A and B are illustrated in different drawings and/or mentioned in different paragraphs, sections or sentences.

Aspects of the Invention

The invention has a number of non-limiting aspects. Non-limiting aspects of the invention include:

1. A method for determining treatment values for ultrasound transmission parameters for use by an ultrasound system comprising a plurality of ultrasound transducers to deliver treatment ultrasound energy that is focused at a target location in the brain of a subject, the method comprising:

determining, based on a model of the head of the subject including the target location and surrounding tissue, intermediate values for each of a plurality of pre-treatment locations;

after placing the plurality of ultrasound transducers in treatment locations for delivery of ultrasound energy into the brain of the subject, determining treatment values for transmission parameters for the plurality of ultrasound transducers based at least in part on the intermediate values.

2. The method of aspect 1 or any other aspect herein wherein determining the intermediate values for each of the plurality of pre-treatment locations is performed prior to placing the plurality of ultrasound transducers in the treatment locations for delivery of ultrasound energy into the brain of the subject.

3. The method of aspect 2 or any other aspect herein wherein determining the treatment values for the transmission parameters for the plurality of ultrasound transducers comprises, for each ultrasound transducer, determining corresponding treatment values based at least in part on the intermediate values for two or more pre-treatment locations.

4. The method of any one of aspects 2 to 3 or any other aspect herein comprising, after placing the plurality of ultrasound transducers in the treatment locations for delivery of ultrasound energy into the brain of the subject, determining the treatment locations of the plurality of ultrasound transducers and wherein determining the treatment values for the transmission parameters for the plurality of ultrasound transducers is based at least in part on the determined treatment locations.

5. The method of aspect 4 or any other aspect herein wherein determining the treatment locations of the plurality of ultrasound transducers comprises determining a treatment position of a structure that supports the plurality of ultrasound transducers and determining the treatment locations of the plurality of ultrasound transducers based on known positional relationships between the structure and the plurality of ultrasound transducers.

6. The method of any one of aspects 2 to 5 or any other aspect herein wherein determining the treatment values for the transmission parameters for the plurality of ultrasound transducers is based at least in part on one or more of the plurality of pre-treatment locations.

7. The method of any one of aspects 2 to 6 or any other aspect herein wherein determining intermediate values for each of a plurality of pre-treatment locations comprises, for each pre-treatment location, simulating propagation of an acoustic wave from the target location to the pre-treatment location to determine an amplitude and phase of the acoustic wave at the pre-treatment location.

8. The method of aspect 7 or any other aspect herein wherein the intermediate values are intermediate values for simulation parameters which, for each pre-treatment location, comprise the amplitude and phase of the acoustic wave at the pre-treatment location.

9. The method of aspect 7 or any other aspect herein wherein determining intermediate values for each of a plurality of pre-treatment locations comprises, for each pre-treatment location, further processing the amplitude and phase of the acoustic wave at the pre-treatment location to obtain intermediate values for transmission parameters which comprise a phase offset and amplitude scaling factor which would cause ultrasound waves originating from the pre-treatment locations to be focused at the target location.

The method of any one of aspects 1 to 9 or any other aspect herein wherein determining treatment values for transmission parameters for the plurality of ultrasound transducers comprises, for each ultrasound transducer, determining corresponding treatment values, wherein determining corresponding treatment values comprises interpolating intermediate values corresponding to a set of pre-treatment locations.

11. The method of aspect 10 or any other aspect herein wherein the set of pre-treatment locations is based at least in part on the treatment location of the ultrasound transducer.

12. The method of any one of aspects 10 to 11 or any other aspect herein wherein the set of pre-treatment locations comprises a number of pre-treatment locations that are nearest neighbors to the treatment location of the ultrasound transducer.

13. The method of any one of aspects 1 to 9 or any other aspect herein wherein determining treatment values for transmission parameters for the plurality of ultrasound transducers comprises, for each ultrasound transducer, determining corresponding treatment values, wherein determining corresponding treatment values comprises performing a Kirchhoff Helmholtz integral (KHI).

14. The method of aspect 13 or any other aspect herein wherein performing the KHI is based at least in part on the treatment location of the ultrasound transducer, at least some of the intermediate values and at least some of the pre-treatment locations.

15. The method of any one of aspects 13 to 14 or any other aspect herein wherein the KHI has a form:

$$\breve{p}(r) = j \int \breve{p}(r') \cos \emptyset \, (r, r') \left(1 - \frac{j}{k(r-r')}\right) \frac{e^{-jk(r-r')}}{\lambda(r-r')} dS' \quad (1)$$

where:

S' is a pre-treatment surface on which the pre-treatment locations are located;

r' are the pre-treatment locations on the surface S';

$\breve{p}(r')$ are complex ultrasound pressures corresponding to the intermediate values at locations r';

r are the treatment locations;

r-r' is the magnitude of the vector $\overrightarrow{r'r}$ pointing from a position r' to a position r;

cos $\emptyset(r,r')$ is a cosine of the angle $\emptyset(r,r')$ between a vector normal to the surface S' and the vector $\overrightarrow{r'r}$;

$\lambda$ is a wavelength of treatment ultrasound energy;

$$k = \frac{2\pi}{\lambda}$$

is a wavenumber of the treatment ultrasound energy; and $\breve{p}(r)$ is complex ultrasound pressure at the treatment location r.

16. The method of any one of aspects 10 to 15 or any other aspect herein wherein the intermediate values comprise simulation parameters and wherein determining corresponding treatment values comprises:

determining pre-cursor treatment values which are simulation parameters representative of the amplitude and phase of an acoustic wave propagating from the target location to the treatment location of the corresponding transducer; and converting the pre-cursor treatment values into the corresponding treatment values which comprise a phase offset and amplitude scaling factor which would cause ultrasound waves originating from the treatment locations of the plurality of ultrasound transducers to be focused at the target location.

17. The method of any one of aspects 1 to 16 or any other aspect herein comprising:

after placing the plurality of ultrasound transducers in the treatment locations for delivery of ultrasound energy into the brain of the subject, determining the treatment locations of the plurality of ultrasound transducers and wherein determining the treatment values for the transmission parameters for the plurality of ultrasound transducers is based at least in part on the determined treatment locations; and repeating the steps of determining the treatment locations of the plurality of ultrasound transducers and determining the treatment values for the transmission parameters for the plurality of ultrasound transducers.

18. The method of aspect 17 or any other aspect herein wherein repeating the steps of determining the treatment locations of the plurality of ultrasound transducers and determining the treatment values for the transmission parameters for the plurality of ultrasound transducers is performed while delivering treatment ultrasound energy to the subject based on the determined treatment values.

19. The method of any one of aspects 17 to 18 or any other aspect herein wherein repeating the steps of determining the treatment locations of the plurality of ultrasound transducers and determining the treatment values for the transmission parameters for the plurality of ultrasound transducers is performed while continuously delivering treatment ultrasound energy to the subject based on the determined treatment values without interruption.

20. The method of any one of aspects 17 to 19 or any other aspect herein wherein repeating the steps of determining the treatment locations of the plurality of ultrasound transducers and determining the treatment values for the transmission parameters for the plurality of ultrasound transducers is performed in real time within one treatment period.

21. The method of any one of aspects 17 to 20 or any other aspect herein wherein repeating the steps of determining the treatment locations of the plurality of ultrasound transducers and determining the treatment values for the transmission parameters for the plurality of ultrasound transducers is performed in response to feedback indicating that the treatment location of one or more of the plurality of ultrasound transducers has changed.

22. The method of aspect 21 or any other aspect herein wherein the feedback indicating that the treatment location of one or more of the plurality of ultrasound transducers has changed comprises feedback indicating that the treatment location of one or more of the plurality of ultrasound transducers has changed by more than a threshold amount.

23. The method of any one of aspects 21 to 22 or any other aspect herein wherein the feedback indicating that the treatment location of one or more of the plurality of ultrasound transducers has changed is provided by a proximity sensor.

24. The method of any one of aspects 17 to 23 or any other aspect herein comprising discontinuing delivery of treatment ultrasound energy to the subject in response to feedback indicating that the treatment location of one or more of the plurality of ultrasound transducers has changed by more than a suspension threshold amount.

25. The method of aspect 24 or any other aspect herein comprising, after discontinuing delivery of treatment ultrasound energy to the subject:
   determining new treatment locations for the plurality of ultrasound transducers;
   determining new treatment values for transmission parameters for the plurality of ultrasound transducers based at least in part on the intermediate values and the new treatment locations; and
   restarting delivering treatment ultrasound energy to the target location in the brain of the subject based on the determined new treatment values.

26. The method of any one of aspects 16 to 25 or any other aspect herein wherein determining the treatment locations of the plurality of ultrasound transducers comprises determining a treatment position of a structure that supports the plurality of ultrasound transducers and determining the treatment locations of the plurality of ultrasound transducers based on known positional relationships between the structure and the plurality of ultrasound transducers.

27. The method of any one aspects 1 to 16 or any other aspect herein comprising delivering treatment ultrasound energy to the target location in the brain of the subject based on the determined treatment values for the ultrasound transmission parameters for the plurality of ultrasound transducers.

28. The method of aspect 27 or any other aspect herein wherein delivering treatment ultrasound energy to the subject causes opening of a blood brain barrier.

29. The method of any one of aspects 27 to 28 or any other aspect herein comprising, while delivering treatment ultrasound energy to the subject based on the determined treatment values for the ultrasound transmission parameters for the plurality of ultrasound transducers, determining second treatment values for transmission parameters for a second plurality of ultrasound transducers based at least in part on the intermediate values wherein such second treatment values for the second plurality of ultrasound transducers would cause treatment ultrasound energy emitted from the second plurality of ultrasound transducers to be focused at a second target location in the brain of the subject.

30. The method of aspect 29 or any other aspect herein wherein the second target is different from the target.

31. The method of any one of aspects 29 to 30 or any other aspect herein wherein the second plurality of ultrasound transducers is different than the plurality of ultrasound transducers.

32. The method of any one of aspects 27 to 28 or any other aspect herein comprising:
   obtaining feedback relating to changes in the treatment locations of one or more of the plurality of ultrasound transducers;
   adjusting the treatment values for the transmission parameters for the plurality of ultrasound transducers in response to the feedback and based at least in part on the intermediate values; and
   delivering treatment ultrasound energy to the subject based on the adjusted treatment values.

33. The method of aspect 32 or any other aspect herein comprising continuously delivering treatment ultrasound energy to the subject based on either the determined treatment values or the adjusted treatment values without interruption.

34. The method of any one of aspects 32 to 33 or any other aspect herein wherein the steps of adjusting the treatment values for the transmission parameters for the plurality of ultrasound transducers in response to the feedback delivering treatment ultrasound energy to the subject based on the adjusted treatment values are performed in real time within one treatment period.

35. The method of any one of aspects 32 to 34 or any other aspect herein wherein obtaining the feedback relating to changes in the treatment locations of one or more of the plurality of ultrasound transducers comprises obtaining feedback indicating that the treatment location of one or more of the plurality of ultrasound transducers has changed by more than a threshold amount.

36. The method of any one of aspects 32 to 35 or any other aspect herein wherein the feedback relating to changes in the treatment locations of one or more of the plurality of ultrasound transducers is provided by a proximity sensor.

37. The method of any one of aspects 32 to 36 or any other aspect herein wherein adjusting the treatment values for the transmission parameters for the plurality of ultrasound transducers comprises:
   determining updated treatment locations for one or more of the plurality of ultrasound transducers; and
   adjusting the treatment values for the transmission parameters for the plurality of ultrasound transducers based at least in part on the updated treatment locations.

38. The method of aspect 37 or any other aspect herein wherein determining the updated treatment locations for the one or more of the plurality of ultrasound transducers comprises determining a treatment position of a structure that supports the plurality of ultrasound transducers and determining the updated treatment locations of the plurality of ultrasound transducers based on known positional relationships between the structure and the plurality of ultrasound transducers.

39. The method of any one of aspects 32 to 38 or any other aspect herein comprising discontinuing delivery of treatment ultrasound energy to the subject in response to feedback indicating that the treatment location of one or more of the plurality of ultrasound transducers has changed by more than a suspension threshold amount.

40. The method of aspect 39 or any other aspect herein comprising, after discontinuing delivery of treatment ultrasound energy to the subject:

determining new treatment locations for the plurality of ultrasound transducers;

determining new treatment values for transmission parameters for the plurality of ultrasound transducers based at least in part on the intermediate values and the new treatment locations; and restarting delivering treatment ultrasound energy to the subject based on the determined new treatment values.

41. A method for delivering treatment ultrasound energy that is focused at a target location in the brain of a subject using an ultrasound system comprising a plurality of ultrasound transducers, the method comprising:

determining treatment values for ultrasound transmission parameters for the plurality of ultrasound transducers using the methods of any one of aspects 1 to 16; and delivering treatment ultrasound energy to the subject based on the determined treatment values for the ultrasound transmission parameters for the plurality of ultrasound transducers.

42. The method of aspect 41 comprising any of the features, combination of features or sub-combinations of features of any of aspects 17 to 40.

43. A system for determining treatment values for ultrasound transmission parameters for use by an ultrasound apparatus comprising a plurality of ultrasound transducers to deliver treatment ultrasound energy that is focused at a target location in the brain of a subject, the system comprising a controller configured to:

determine, based on a model of the subject including the target location and surrounding tissue, intermediate values for each of a plurality of pre-treatment locations;

determine, after placing the plurality of ultrasound transducers in treatment locations for delivery of ultrasound energy into the brain of the subject, treatment values for transmission parameters for the plurality of ultrasound transducers based at least in part on the intermediate values.

44. The system of aspect 43 wherein the controller is configured to perform any of the features, combination of features or sub-combinations of features of any of aspects 1 to 40.

45. An ultrasound system for delivering treatment ultrasound energy that is focused at a target location in the brain of a subject, the ultrasound system comprising:

a plurality of ultrasound transducers;

a controller configured to:

determine treatment values for ultrasound transmission parameters for the plurality of ultrasound transducers using the methods of any one of aspects 1 to 16; and cause delivery of treatment ultrasound energy to the subject based on the determined treatment values for the ultrasound transmission parameters for the plurality of ultrasound transducers.

46. The system of aspect 45 comprising any of the features, combination of features or sub-combinations of features of any of aspects 17 to 40.

47. A method for determining expected values of receive parameters of ultrasound energy focused at, and reflected from, a target location in the brain of a subject and received at a receive ultrasound transducer, the method comprising:

determining, based on a model of the head of the subject including the target location and surrounding tissue, intermediate values for each of a plurality of pre-treatment locations;

after placing receive ultrasound transducer in a receive location for receiving reflected ultrasound energy from the target location, determining expected values of the receive parameters for the receive ultrasound transducer based at least in part on the intermediate values.

48. The method of aspect 47 or any other aspect herein wherein determining the intermediate values for each of the plurality of pre-treatment locations is performed prior to placing the receive ultrasound transducer in the receive location.

49. The method of aspect 48 or any other aspect herein wherein determining expected values of the receive parameters for the receive ultrasound transducer comprises determining the expected values based at least in part on the intermediate values for two or more pre-treatment locations.

50. The method of any one of aspects 48 to 49 or any other aspect herein comprising, after placing the receive ultrasound transducer in the receive location, determining the receive location of the receive ultrasound transducer and wherein determining the expected values of the receive parameters for the receive ultrasound transducer is based at least in part on the determined receive location.

51. The method of aspect 50 or any other aspect herein wherein determining the expected values of the receive parameters for the receive ultrasound transducer comprises determining a treatment position of a structure that supports the receive ultrasound transducer and determining the receive location based on a known positional relationship between the structure and the receive transducer.

52. The method of any one of aspects 48 to 51 or any other aspect herein wherein determining the expected values of the receive parameters for the receive transducer is based at least in part on one or more of the plurality of pre-treatment locations.

53. The method of any one of aspects 48 to 52 or any other aspect herein wherein determining intermediate values for each of a plurality of pre-treatment locations comprises, for each pre-treatment location, simulating propagation of an acoustic wave from the target location to the pre-treatment location to determine an amplitude and phase of the acoustic wave at the pre-treatment location.

54. The method of any one of aspects 47 to 53 or any other aspect herein wherein determining the expected values of the receive parameters for the receive ultrasound transducer comprises interpolating intermediate values corresponding to a set of pre-treatment locations.

55. The method of aspect 54 or any other aspect herein wherein the set of pre-treatment locations is based at least in part on the receive location.

56. The method of any one of aspects 54 to 55 or any other aspect herein wherein the set of pre-treatment locations comprises a number of pre-treatment locations that are nearest neighbors to the receive location.

57. The method of any one of aspects 47 to 53 or any other aspect herein wherein determining the expected values of the receive parameters for the receive ultrasound transducer comprises performing a Kirchhoff Helmholtz integral (KHI).

58. The method of aspect 57 or any other aspect herein wherein performing the KHI is based at least in part on the receive location, at least some of the intermediate values and at least some of the pre-treatment locations.

59. The method of any one of aspects 57 to 58 or any other aspect herein wherein the KHI has a form:

$$\breve{p}(r) = j \int \breve{p}(r') \cos \phi \ (r, r')\left(1 - \frac{j}{k(r-r')}\right)\frac{e^{-jk(r-r')}}{\lambda(r-r')}dS' \qquad (1)$$

where:

S' is a pre-treatment surface on which the pre-treatment locations are located;

r' are the pre-treatment locations on the surface S';

$\breve{p}(r')$ are complex ultrasound pressures corresponding to the intermediate values at locations r';

r is the receive location;

r-r' is the magnitude of the vector $\overrightarrow{r'r}$ pointing from a position r' to a position r;

cos $\phi$(r,r') is a cosine of the angle $\phi$(r,r') between a vector normal to the surface S' and the vector $\overrightarrow{r'r}$;

$\lambda$ is a wavelength of ultrasound energy;

$$k = \frac{2\pi}{\lambda}$$

is a wavenumber of the ultrasound energy; and $\breve{p}(r)$ is complex ultrasound pressure at the receive location r.

60. A system for determining expected values of receive parameters of ultrasound energy focused at, and reflected from, a target location in the brain of a subject and received at a receive ultrasound transducer, the system comprising a controller configured to:

determine, based on a model of the head of the subject including the target location and surrounding tissue, intermediate values for each of a plurality of pre-treatment locations;

determine, after placing receive ultrasound transducer in a receive location for receiving reflected ultrasound energy from the target location, expected values of the receive parameters for the receive ultrasound transducer based at least in part on the intermediate values.

61. The system of aspect 60 wherein the controller is configured to perform any of the features, combination of features or sub-combinations of features of any of aspects 47 to 59.

62. Method comprising any features, combinations of features and/or sub-combinations of features disclosed herein.

63. Apparatus comprising any features, combinations of features and/or sub-combinations of features disclosed herein.

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples, but should be given the broadest interpretation consistent with the description as a whole.

What is claimed is:

1. A method for determining treatment values for ultrasound transmission parameters for use by an ultrasound system comprising a plurality of ultrasound transducers to deliver treatment ultrasound energy that is focused at a target location in a brain of a subject, the method comprising:

determining, before placing the plurality of transducers in treatment locations for delivery of ultrasound energy in the brain of the subject and based on a model of a head of the subject including the target location and surrounding tissue, intermediate values for each of a plurality of pre-treatment locations;

after placing the plurality of ultrasound transducers in treatment locations for delivery of ultrasound energy into the brain of the subject and before delivering treatment ultrasound energy to the subject, determining treatment values for transmission parameters for the plurality of ultrasound transducers, wherein determining the treatment values for each ultrasound transducer is based at least in part on; two or more pre-treatment locations, the intermediate values for the two or more pre-treatment locations and the treatment location for the ultrasound transducer; and communicating the treatment values for the transmission parameters for the plurality of ultrasound transducers to the ultrasound system, thereby enabling the ultrasound system to deliver treatment ultrasound energy, based on the treatment values for the transmission parameters for the plurality of ultrasound transducers, to thereby deliver treatment ultrasound energy that is focused at the target location in the brain of the subject;

wherein the pre-treatment locations are different than the treatment locations for delivery of ultrasound energy into the brain of the subject.

2. The method of claim 1 comprising, after placing the plurality of ultrasound transducers in the treatment locations for delivery of ultrasound energy into the brain of the subject, determining the treatment locations of the plurality of ultrasound transducers and wherein determining the treatment values for the transmission parameters for the plurality of ultrasound transducers is based at least in part on the determined treatment locations.

3. The method of claim 1 wherein determining intermediate values for each of a plurality of pre-treatment locations comprises, for each pre-treatment location, simulating propagation of an acoustic wave from the target location to the pre-treatment location to determine an amplitude and phase of the acoustic wave at the pre-treatment location.

4. The method of claim 3 wherein determining intermediate values for each of a plurality of pre-treatment locations comprises, for each pre-treatment location, further processing the amplitude and phase of the acoustic wave at the pre-treatment location to obtain intermediate values for transmission parameters which comprise a phase offset and amplitude scaling factor which would cause ultrasound waves originating from the pre-treatment locations to be focused at the target location.

5. The method of claim 1 wherein determining the treatment values for each ultrasound transducer comprises: determining a nearest neighbor plurality of pre-treatment locations that are proximate to the treatment location for the transducer; interpolating the intermediate values for the nearest neighbor plurality of pre-treatment locations to determine the treatment value for the ultrasound transducer, wherein the interpolating is based at least in part on: the intermediate values for the nearest neighbor plurality of pre-treatment locations and a difference between the treatment location for the ultrasound transducer and each of the nearest neighbor plurality of pre-treatment locations.

6. The method of claim 5 comprising determining the treatment locations of the plurality of ultrasound transducers based at least in part on measurement of a structure that supports the plurality of transducers in their treatment locations and wherein the interpolating is based at least in part on a difference between the determined treatment location and each of the nearest neighbor plurality of pre-treatment locations.

7. The method of claim 5 wherein determining the nearest neighbor plurality of pre-treatment locations comprises determining eight pre-treatment locations that are nearest neighbors to the treatment location of the ultrasound transducer.

8. The method of claim 5 wherein the intermediate values comprise simulation parameters and wherein determining the treatment values for each ultrasound transducer comprises:

determining pre-cursor treatment values which are simulation parameters representative of an amplitude and phase of an acoustic wave propagating from the target location to the treatment location of the ultrasound transducer; and converting the pre-cursor treatment values into the corresponding treatment values which comprise a phase offset and amplitude scaling factor which would cause ultrasound waves originating from the treatment location of the ultrasound transducer to be focused at the target location.

9. The method of claim 1 comprising:

after placing the plurality of ultrasound transducers in the treatment locations for delivery of ultrasound energy into the brain of the subject, determining updated treatment locations of the plurality of ultrasound transducers based at least in part on measurement and wherein determining the treatment values for the transmission parameters for the plurality of ultrasound transducers is based at least in part on the determined updated treatment locations; and repeating the steps of determining the updated treatment locations of the plurality of ultrasound transducers and determining the treatment values for the transmission parameters for the plurality of ultrasound transducers.

10. The method of claim 9 wherein repeating the steps of determining the updated treatment locations of the plurality of ultrasound transducers and determining the treatment values for the transmission parameters for the plurality of ultrasound transducers is performed while delivering treatment ultrasound energy to the subject based on the determined treatment values.

11. The method of claim 9 wherein repeating the steps of determining the updated treatment locations of the plurality of ultrasound transducers and determining the treatment values for the transmission parameters for the plurality of ultrasound transducers is performed while continuously delivering treatment ultrasound energy to the subject based on the determined treatment values without interruption.

12. The method of claim 9 wherein repeating the steps of determining the updated treatment locations of the plurality of ultrasound transducers and determining the treatment values for the transmission parameters for the plurality of ultrasound transducers is performed in real time within one treatment period.

13. The method of claim 9 wherein repeating the steps of determining the updated treatment locations of the plurality of ultrasound transducers and determining the treatment values for the transmission parameters for the plurality of ultrasound transducers is performed in response to feedback indicating that the treatment location of one or more of the plurality of ultrasound transducers has changed.

14. The method of claim 9 comprising discontinuing delivery of treatment ultrasound energy to the subject in response to feedback indicating that the treatment location of one or more of the plurality of ultrasound transducers has changed by more than a suspension threshold amount and, after discontinuing delivery of treatment ultrasound energy to the subject:

determining new updated treatment locations for the plurality of ultrasound transducers;

determining new treatment values for transmission parameters for the plurality of ultrasound transducers based at least in part on the intermediate values and the new updated treatment locations; and restarting delivering treatment ultrasound energy to the target location in the brain of the subject based on the determined new treatment values.

15. The method of claim 1 comprising delivering treatment ultrasound energy to the target location in the brain of the subject based on the determined treatment values for the ultrasound transmission parameters for the plurality of ultrasound transducers.

16. A system for determining treatment values for ultrasound transmission parameters for use by an ultrasound apparatus comprising a plurality of ultrasound transducers to deliver treatment ultrasound energy that is focused at a target location in a brain of a subject, the system comprising a controller configured to:

determine, before placing the plurality of transducers in treatment locations for delivery of ultrasound energy in the brain of the subject and based on a model of a head of the subject including the target location and surrounding tissue, intermediate values for each of a plurality of pre-treatment locations;

determine, after placing the plurality of ultrasound transducers in the treatment locations for delivery of ultrasound energy into the brain of the subject and before delivering treatment ultrasound energy to the subject, treatment values for transmission parameters for the plurality of ultrasound transducers, wherein determining the treatment values for each ultrasound transducer is based at least in part on: two or more pre-treatment locations, the intermediate values for the two or more pre-treatment locations and the treatment location for the ultrasound transducer; and communicate the treatment values for the transmission parameters for the plurality of ultrasound transducers to the ultrasound apparatus, thereby enabling the ultrasound apparatus to deliver treatment ultrasound energy, based on the treatment values for the transmission parameters for the plurality of ultrasound transducers, to thereby deliver treatment ultrasound energy that is focused at the target location in the brain of the subject;

wherein the pre-treatment locations are different than the treatment locations for delivery of ultrasound energy into the brain of the subject.

17. The system according to claim 16 wherein the controller is configured to:

after placing the plurality of ultrasound transducers in the treatment locations for delivery of ultrasound energy into the brain of the subject, determine updated treatment locations of the plurality of ultrasound transducers based at least in part on measurement and determine the treatment values for the transmission parameters for the plurality of ultrasound transducers based at least in part on the determined updated treatment locations; and repeat the steps of determining the updated treatment locations of the plurality of ultrasound transducers and determining the treatment values for the transmission parameters for the plurality of ultrasound transducers.

* * * * *